(12) United States Patent
Lu et al.

(10) Patent No.: US 7,939,548 B2
(45) Date of Patent: May 10, 2011

(54) CERTAIN CHEMICAL ENTITIES, COMPOSITIONS, AND METHODS

(75) Inventors: Pu-Ping Lu, Foster City, CA (US); Xiangping Qian, Foster City, CA (US); Chihyuan (Grace) Chuang, San Mateo, CA (US); Bradley P. Morgan, Moraga, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 797 days.

(21) Appl. No.: 11/888,647

(22) Filed: Jul. 31, 2007

(65) Prior Publication Data

US 2008/0132545 A1 Jun. 5, 2008

Related U.S. Application Data

(60) Provisional application No. 60/835,236, filed on Aug. 2, 2006.

(51) Int. Cl.
*A61K 31/444* (2006.01)
*C07D 401/12* (2006.01)
*C07D 213/80* (2006.01)
(52) U.S. Cl. ........ 514/334; 514/332; 514/344; 514/352; 546/258; 546/262; 546/289; 546/310
(58) Field of Classification Search ........................ None
See application file for complete search history.

(56) References Cited

U.S. PATENT DOCUMENTS

| 4,140,853 | A | 2/1979 | Vorbrueggen |
| 6,878,714 | B2 * | 4/2005 | Askew et al. ................. 514/256 |
| 2003/0229089 | A1 | 12/2003 | Yamada et al. |
| 2008/0139575 | A1 | 6/2008 | Lu et al. |
| 2008/0146619 | A1 | 6/2008 | Lu et al. |
| 2009/0012126 | A1 | 1/2009 | Lu et al. |

FOREIGN PATENT DOCUMENTS

| WO | WO 98/21199 | | 5/1998 |
| WO | WO 2005/108391 | A1 | 11/2005 |
| WO | WO 2008/016643 | A2 | 2/2008 |

OTHER PUBLICATIONS

International Search Report mailed on Apr. 7, 2008, for PCT Application Publication No. WO 2008/016643 A2, published on Feb. 7, 2008.
U.S. Appl. No. 11/888,672—Non-final Office Action dated Jul. 26, 2010.
U.S. Appl. No. 11/888,655—Non-final Office Action dated Jul. 27, 2010.
U.S. Appl. No. 11/888,625—Non-final Office Action dated Jul. 27, 2010.

\* cited by examiner

*Primary Examiner* — Zinna N Davis
(74) *Attorney, Agent, or Firm* — Foley & Lardner LLP

(57) ABSTRACT

Chemical entities that modulate smooth muscle myosin and/or non-muscle myosin, and chemical entities, pharmaceutical compositions and methods of treatment of diseases and conditions associated with smooth muscle myosin and/or non-muscle myosin are described.

36 Claims, No Drawings

CERTAIN CHEMICAL ENTITIES, COMPOSITIONS, AND METHODS

This application claims the benefit of U.S. Provisional Patent Application No. 60/835,236, filed Aug. 2, 2006, which is incorporated herein by reference for all purposes.

Provided are certain substituted heterocycles, including chemical entities that modulate smooth muscle myosin and/or non-muscle myosin, and chemical entities, pharmaceutical compositions and methods of treatment of diseases and conditions associated with smooth muscle myosin and/or non-muscle myosin.

Myosin is present in all muscle and non-muscle cells. Of the ten distinct classes of myosin in human cells, myosin-II is thought to be the form responsible for contraction of skeletal, cardiac, and smooth muscle. Myosin-II is also the isoform present in non-muscle myosins, also known as cytoplasmic myosins. The non-muscle myosins are ubiquitously present in eukaryotic cells, where the smooth muscle myosins are generally present in smooth muscle cells.

Myosin-II is significantly different in amino acid composition and in overall structure from myosins in the other nine distinct classes. Myosin-II consists of two globular head domains, called Subfragment-1 or S1, linked together by a long alpha-helical coiled-coiled tail. Proteolysis of myosin generates either S1 or heavy meromyosin (HMM, a two-headed form with a truncated tail), depending on the proteolysis conditions. S1 contains the ATPase and actin-binding properties of the molecule. S1 has been shown to be sufficient to move actin filaments in vitro, and is therefore likely to be the motor domain of the molecule.

Although myosin-II isoforms from various tissues differ in a number of biological properties, they share the same basic molecular structure as a dimer of two heavy chains (approximately 200 kDa) which are noncovalently associated with two pairs of light chains (approximately 20 and 17 kDa). The two globular amino-terminal heads are tethered together by the carboxy-terminal alpha-helical coiled-coil that forms a tail. The tails are believed to be involved in the assembly of myosin molecules into filaments, whereas the heads are thought to have an actin-activated $Mg^{2+}$-ATPase activity. Each myosin head can be divided by three protease-sensitive regions into peptides of approximately 25, 50, and 20 kDa. The more amino-terminal 25 kDa-50 kDa junction is close to the ATP binding region, whereas the actin-binding domain is near the 50 kDa-20 kDa junction.

S1 consists of a globular actin binding and nucleotide binding region known as the catalytic domain. This domain is attached at its carboxy-terminus to an alpha-helix that has two light chains of about 20 kDa each wrapped around it. This light-chain binding domain of S1 is known as the lever arm. Upon transitioning from the pre-stroke to the post-stroke state, the lever arm is believed to swing through an angle of about 90 degrees about a fulcrum point in the catalytic domain near the nucleotide-binding site. The "power stroke" is driven by the hydrolysis of ATP.

The other end of the myosin molecule is an alpha-helical coiled-coiled tail involved in self assembly of myosin molecules into bipolar thick filaments. These thick filaments interdigitate between thinner actin filaments, and the two filament systems slide past one another during contraction of the muscle. This filament sliding mechanism is thought to involve conformational changes in the myosin heads causing them to walk along the thin actin filaments at the expense of ATP hydrolysis. While non-muscle myosins act in a similar manner, they are understood to slide at a slower velocity than the smooth muscle myosins.

The complete cDNA of the human smooth muscle myosin has been described. The sequence of human smooth muscle myosin is 52% identical to human cardiac myosin in the catalytic S1 region. See, for example, PCT publication No. WO 03/14323.

Provided is at least one chemical entity chosen from compounds of Formula I:

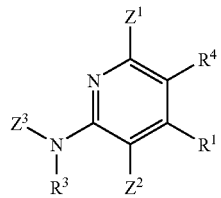

Formula I and pharmaceutically acceptable salts thereof wherein $R^1$ and $R^4$ are independently chosen from hydrogen, cyano, halo, hydroxy, azido, nitro, sulfonyl, sulfinyl, sulfanyl, optionally substituted alkoxy, optionally substituted acyloxy, optionally substituted aminocarbonyloxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted aminocarbonyl, and optionally substituted carbaminodoyl;

$Z^1$ is chosen from hydrogen, cyano, optionally substituted alkyl, optionally substituted acyl, optionally substituted alkoxycarbonyl, optionally substituted amino, optionally substituted aminocarbonyl, optionally substituted carbamimidoyl, optionally substituted alkoxy, optionally substituted aryloxy, optionally substituted heteroaryloxy, optionally substituted heterocycloalkyloxy, optionally substituted alkenyl, optionally substituted alkynyl, sulfonyl, sulfinyl, and sulfanyl;

$Z^2$ is chosen from hydrogen, optionally substituted amidino, carboxyl, optionally substituted alkoxycarbonyl, optionally substituted acyl, optionally substituted alkenyl, optionally substituted alkyl, optionally substituted heterocycloalkyl, optionally substituted heteroaryl, and optionally substituted aminocarbonyl;

$Z^3$ is chosen from optionally substituted alkyl; and $R^3$ is chosen from hydrogen and optionally substituted alkyl.

Also provided is a pharmaceutical composition comprising at least one chemical entity described herein, together with at least one pharmaceutically acceptable vehicle chosen from carriers, adjuvants, and excipients.

Also provided are methods of treatment of one or more diseases associated with smooth muscle myosin, or non-muscle myosin. The methods of treatment comprise administering a therapeutically effective amount of at least one chemical entity provided herein or a pharmaceutical composition comprising at least one chemical entity described herein, together with at least one pharmaceutically acceptable vehicle chosen from carriers, adjuvants, and excipients.

Other aspects and embodiments will be apparent to those skilled in the art from the following detailed description.

As used in the present specification, the following words and phrases are generally intended to have the meanings as set forth below, except to the extent that the context in which they are used indicates otherwise.

The following abbreviations and terms have the indicated meanings throughout:

PIPES=1,4-piperazinediethanesulfonic acid
ATP=adenosine 5'-triphosphate
DTT=DL-dithiothreitol
BSA=bovine serum albumin
NADH=nicotinamide adenine dinucleotide
PEP=phosphoenolpyruvic acid
EGTA=ethylene glycol-bis(2-aminoethylether)-N,N,N',N'-tetraacetic acid
Ac=acetyl
APCI=atmospheric pressure chemical ionization
atm=atomosphere
Boc=tert-butoxycarbonyl
c-=cyclo
CBZ=carbobenzyloxy=benzyloxycarbonyl
CDI=carbonyldiimidazole
DCM=dichloromethane=methylene chloride=$CH_2Cl_2$
DIAD=diisopropyl azodicarboxylate
DIEA=DIPEA=N,N-diisopropylethylamine
DMAP=4-(dimethylamino)pyridine
DMF=N,N-dimethylformamide
DMSO=dimethyl sulfoxide
(DPPF)$PdCl_2$=[1,1'-bis(diphenylphosphino)ferrocene]dichloropalladium(II)
Et=ethyl
EtOAc=ethyl acetate
EtOH=ethanol
g=gram
GC=gas chromatography
h or hr=hour
HATU=O-(7-azabenzotriazol-1-yl)-N,N,N',N'-tetramethyluronium hexafluorophosphate
HBTU=O-(benzotriazol-1-yl)-N,N,N',N'-tetramethyluronium hexafluorophosphate
HOBT=1-hydroxybenzotriazole
HPLC=high pressure liquid chromatography
i-=iso
kg or Kg=kilogram
L or l=liter
LC/MS=LCMS=liquid chromatography-mass spectrometry
LDA=lithium diisopropylamide
LRMS=low resolution mass spectrometry
m/z=mass-to-charge ratio
Me=methyl
NMP=N-Methyl-2-pyrrolidone
NMR=nuclear magnetic resonance
MPLC=medium pressure liquid chromatography
min=minute
mL=milliliter
MW=microwave
n-=normal
Ph=phenyl
$(Ph_3P)_4Pd$=tetrakis(triphenylphosphine)palladium(0)
$(Ph_3P)_2PdCl_2$=dichlorobis(triphenylphosphine)palladium(II)
RP-HPLC=reverse phase-high pressure liquid chromatography
rt or RT=room temperature
s-=sec-=secondary
t-=tert-=tertiary
TBAF=tetrabutylammonium fluoride
TBS=TBDMS=tert-butyldimethylsilyl
TES=triethylsilyl or triethylsilane
TMS=trimethylsilyl or trimethylsilane
TFA=trifluoroacetic acid
THF=tetrahydrofuran
TLC=thin layer chromatography
UV=ultraviolet
Vol=volume equivalent in mL/g or L/Kg or the limiting reagent unless otherwise specified As used herein, when any variable occurs more than one time in a chemical formula, its definition on each occurrence is independent of its definition at every other occurrence.

A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "ATPase," as used herein, refers to an enzyme that is capable of hydrolyzing ATP. ATPases include proteins comprising molecular motors such as myosins.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric combinations having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups havirig one to four carbons.

"Alkenyl" refers to an unsaturated branched or straight-chain alkyl group having at least one carbon-carbon double bond derived by the removal of one hydrogen atom from a single carbon atom of a parent alkene. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkynyl" refers to an unsaturated branched or straight-chain alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to four carbons.

The term "amidino" refers to the group —C(=NH)—NH$_2$. The term "substituted amidino" refers to the formula —C(=NR')—NR"R" in which each of the R" groups is independently chosen from hydrogen, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl and R' is chosen from hydrogen, cyano, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl, provided that at least one R' or R" group is not hydrogen.

"Mono- and di-alkylcarboxamide" encompasses a group of the formula —(C=O)NR$_a$R$_b$ where R$_a$ and R$_b$ are independently chosen from hydrogen and alkyl groups of the indicated number of carbon atoms, provided that R$_a$ and R$_b$ are not both hydrogen.

"Acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a C$_2$ acyl group is an acetyl group having the formula CH$_3$(C=O)—.

"Formyl" refers to the group —C(O)H.

"Carboxy" and/or "carboxyl" refer to the group —C(O)OH.

By "alkoxycarbonyl" is meant a group of the formula (alkoxy)(C=O)— attached through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker.

By "amino" is meant the group —NH$_2$.

"Mono- and di-(alkyl)amino" encompasses secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propylamino.

The term "optionally substituted aminocarbonyl" refers to the group —CONR$^b$R$^c$, where R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently chosen from hydrogen and optionally substituted C$_1$-C$_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

"Aryl" encompasses:

6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "aralkyl" refers to the group -alkyl-aryl.

"Carbamimidoyl" refers to the group —C(=NH)—NH$_2$.

"Substituted carbamimidoyl" refers to the group —C(=NR$^e$)—NR$^f$R$^g$ where R$^e$ is chosen from: hydrogen, cyano, optionally substituted alkyl, optionally substituted cycloalkyl, optionally substituted aryl, optionally substituted heteroaryl, and optionally substituted heterocycloalkyl; and $R^f$ and $R^g$ are independently chosen from: hydrogen optionally substituted alkyl, optionally substituted cycloalkyl, optionally substituted aryl, optionally substituted heteroaryl, and optionally substituted heterocycloalkyl, provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —NR BC(NCN)$NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), optionally substituted aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO2($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:
5- to 7-membered aromatic, monocyclic rings containing one or more, for example, from 1 to 4, or in certain embodiments, from 1 to 3, heteroatoms chosen from N, O, and S, with the remaining ring atoms being carbon;
bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and
tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—$O^-$) substituents, such as pyridinyl N-oxides.

By "heterocycloalkyl" is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—$O^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteratoms independently selected from oxygen, sulfur, and nitrogen and is not aromatic.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "sulfanyl" includes the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

The term "sulfinyl" includes the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S($O_2$)-(optionally substituted ($C_1$-$C_6$)alkyl), —S($O_2$)-optionally substituted aryl), —S($O_2$)-optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-optionally substituted heteroaryloxy), —S($O_2$)-(optionally substituted heterocyclyloxy); and —S($O_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), optionally substituted aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from:

$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), optionally substituted aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), optionally substituted aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_n$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), optionally substituted aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" refers to the group —NHR$^d$ or —NR$^d$R$^e$ wherein R$^d$ is chosen from: hydroxy, optionally substituted alkoxy, optionally substituted alkyl, optionally substituted cycloalkyl, optionally substituted acyl, optionally substituted carbamimidoyl, optionally substituted aminocarbonyl, optionally substituted aryl, optionally substituted heteroaryl, optionally substituted heterocycloalkyl, optionally substituted alkoxycarbonyl, sulfinyl and sulfonyl, and wherein $R^e$ is chosen from: optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

- $-R^a$, $-OR^b$, optionally substituted amino (including $-NR^cCOR^b$, $-NR^cCO_2R^a$, $-NR^cCONR^bR^c$, $-NR^bC(NR^c)NR^bR^c$, $-NR^bC(NCN)NR^bR^c$, and $-NR^cSO_2R^a$), halo, cyano, nitro, oxo (as a substitutent for cycloalkyl, heterocycloalkyl, and heteroaryl), optionally substituted acyl (such as $-COR^b$), optionally substituted alkoxycarbonyl (such as $-CO_2R^b$), optionally substituted aminocarbonyl (such as $-CONR^bR^c$), $-OCOR^b$, $-OCO_2R^a$, $-OCONR^bR^c$, $-OP(O)(OR^b)OR^c$, sulfanyl (such as $SR^b$), sulfinyl (such as $-SOR^a$), and sulfonyl (such as $-SO_2R^a$ and $-SO_2NR^bR^c$),
- where $R^a$ is chosen from optionally substituted $C_1$-$C_6$ alkyl, optionally substituted alkenyl, optionally substituted alkynyl, optionally substituted aryl, and optionally substituted heteroaryl;
- $R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and
- $R^c$ is independently chosen from hydrogen and optionally substituted $C_1$-$C_4$ alkyl; or
- $R^b$ and $R^c$, and the nitrogen to which they are attached, form an optionally substituted heterocycloalkyl group; and
- where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, $-OC_1$-$C_4$ alkyl, $-OC_1$-$C_4$ alkylphenyl, $-C_1$-$C_4$ alkyl-OH, $-OC_1$-$C_4$ haloalkyl, halo, $-OH$, $-NH_2$, $-C_1$-$C_4$ alkyl-$NH_2$, $-N(C_1$-$C_4$ alkyl)($C_1$-$C_4$ alkyl), $-NH(C_1$-$C_4$ alkyl), $-N(C_1$-$C_4$ alkyl)($C_1$-$C_4$ alkylphenyl), $-NH(C_1$-$C_4$ alkylphenyl), cyano, nitro, oxo (as a substituent for cycloalkyl, heterocycloalkyl, or heteroaryl), $-CO_2H$, $-C(O)OC_1$-$C_4$ alkyl, $-CON(C_1$-$C_4$ alkyl)($C_1$-$C_4$ alkyl), $-CONH(C_1$-$C_4$ alkyl), $-CONH_2$, $-NHC(O)(C_1$-$C_4$ alkyl), $-NHC(O)(phenyl)$, $-N(C_1$-$C_4$ alkyl)C(O)($C_1$-$C_4$ alkyl), $-N(C_1$-$C_4$ alkyl)C(O)(phenyl), $-C(O)C_1$-$C_4$ alkyl, $-C(O)C_1$-$C_4$ alkylphenyl, $-C(O)C_1$-$C_4$ haloalkyl, $-OC(O)C_1$-$C_4$ alkyl, $-SO_2(C_1$-$C_4$ alkyl), $-SO_2(phenyl)$, $-SO_2(C_1$-$C_4$ haloalkyl), $-SO_2NH_2$, $-SO_2NH(C_1$-$C_4$ alkyl), $-SO_2NH(phenyl)$, $-NHSO_2(C_1$-$C_4$ alkyl), $-NHSO_2(phenyl)$, and $-NHSO_2(C_1$-$C_4$ haloalkyl); and
- wherein optionally substituted acyl, optionally substituted alkoxycarbonyl, sulfinyl and sulfonyl are as defined herein.

The term "substituted amino" also refers to N-oxides of the groups $-NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula I exists in various tautomeric forms, chemical entities described herein include all tautomeric forms of the compound.

Chemical entities described herein include, but are not limited to compounds of Formula I and all pharmaceutically acceptable forms thereof. Pharmaceutically acceptable forms of the chemical entities recited herein include pharmaceutically acceptable salts, solvates, crystal forms (including polymorphs and clathrates), chelates, non-covalent complexes, prodrugs, and mixtures thereof. In certain embodiments, the chemical entities described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any chemical entities that become compounds of Formula I when administered to a patient, e.g., upon metabolic processing of the prodrug. Examples of prodrugs include, but are not limited to, acetate, formate, phosphate, and benzoate and like derivatives of functional groups (such as alcohol or amine groups) in the compounds of Formula I.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example an active agent may be an anti-cancer therapeutic.

By "significant" is meant any detectable change that is statistically significant in a standard parametric test of statistical significance such as Student's T-test, where p<0.05.

The term "therapeutically effective amount" of a chemical entity described herein means an amount effective, when administered to a human or non-human patient, to provide a therapeutic benefit such as amelioration of symptoms, slowing of disease progression, or prevention of disease.

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Patient" refers to an animal, such as a mammal, that has been or will be the object of treatment, observation or experiment. The methods described herein can be useful in both human therapy and veterinary applications. In some embodiments, the patient is a mammal; in some embodiments the patient is human; and in some embodiments the patient is chosen from cats and dogs.

Provided is at least one chemical entity chosen from compounds of Formula I

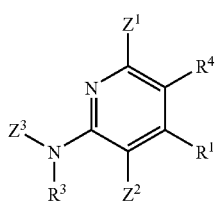

Formula I and pharmaceutically acceptable salts thereof wherein
$R^1$ and $R^4$ are independently chosen from hydrogen, cyano, halo, hydroxy, azido, nitro, sulfonyl, sulfinyl, sulfanyl, optionally substituted alkoxy, optionally substituted acyloxy, optionally substituted aminocarbonyloxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted aminocarbonyl, and optionally substituted carbaminodoyl;

$Z^1$ is chosen from hydrogen, cyano, optionally substituted alkyl, optionally substituted acyl, optionally substituted alkoxycarbonyl, optionally substituted amino, optionally substituted aminocarbonyl, optionally substituted carbamimidoyl, optionally substituted alkoxy, optionally substituted aryloxy, optionally substituted heteroaryloxy, optionally substituted heterocycloalkyloxy, optionally substituted alkenyl, optionally substituted alkynyl, sulfonyl, sulfinyl, and sulfanyl;

$Z^2$ is chosen from hydrogen, optionally substituted amidino, carboxyl, optionally substituted alkoxycarbonyl, optionally substituted acyl, optionally substituted alkenyl, optionally substituted alkyl, optionally substituted heterocycloalkyl, optionally substituted heteroaryl, and optionally substituted aminocarbonyl;

$Z^3$ is chosen from optionally substituted alkyl; and $R^3$ is chosen from hydrogen and optionally substituted alkyl.

In certain embodiments, $Z^2$ is chosen from carboxyl, optionally substituted alkoxycarbonyl, optionally substituted acyl, optionally substituted alkenyl, and optionally substituted alkyl.

In certain embodiments, $Z^2$ is chosen from carboxyl, optionally substituted piperidinylcarbonyl, optionally substituted pyridinylcarbonyl, optionally substituted lower alkyl, optionally substituted lower alkenyl, and lower alkoxycarbonyl.

In certain embodiments, $Z^2$ is chosen from (2-(N-acetylaminomethyl) piperidin-1-yl)carbonyl; (2-aminomethylpiperidin-1-yl)carbonyl; 1-hydroxy -2-amino-ethyl; 2-((methylsulfonamido)methyl)piperidin-1-ylcarbonyl; 2-(methylaminocarbonyl)ethenyl; 2-(pyridin-3-ylmethyl)-2H-tetrazol-5-ylmethyl; aminomethyl; carboxyl; methoxycarbonyl; pyridin-2-ylcarbonyl; pyridin-3-ylcarbonyl; and pyridin-4-ylcarbonyl.

In certain embodiments, $R^3$ is chosen from hydrogen and optionally substituted lower alkyl. In certain embodiments, $R^3$ is chosen from hydrogen and lower alkyl. In certain embodiments, $R^3$ is chosen from hydrogen and methyl. In certain embodiments, $R^3$ is hydrogen.

In certain embodiments, $R^4$ is chosen from hydrogen, cyano, halo, azido, optionally substituted aminocarbonyl, and optionally substituted alkyl. In certain embodiments, $R^4$ is chosen from hydrogen, cyano, chloro, bromo, fluoro, azido, optionally substituted alkylaminocarbonyl, and optionally substituted methyl. In certain embodiments, $R^4$ is chosen from hydrogen, cyano, chloro, bromo, azido, pyridin-3-ylmethylaminocarbonyl, aminomethyl, and hydroxymethyl. In certain embodiments, $R^4$ is hydrogen.

In certain embodiments, $R^5$ is chosen from hydrogen and lower alkyl. In certain embodiments, $R^5$ is chosen from hydrogen and methyl. In certain embodiments, $R^5$ is hydrogen.

In certain embodiments, $Z^2$ is —C(O)—NR$^2$R$^5$ wherein $R^2$ is chosen from optionally substituted alkyl and optionally substituted cycloalkyl; and $R^5$ is chosen from hydrogen and optionally substituted alkyl.

In certain embodiments, $R^2$ is chosen from optionally substituted methyl, optionally substituted ethyl, optionally substituted propyl, optionally substituted butyl, optionally substituted pentyl, optionally substituted hexyl, optionally substituted cyclopropyl, optionally substituted cyclopentyl, and optionally substituted cyclohexyl where each optionally substituted group is optionally substituted with one, two or three groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments, $R^2$ is chosen from methyl and ethyl, where the methyl and ethyl groups are optionally substituted with one or two groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments, $R^2$ is chosen from (1-(2-aminoethyl)-1H-pyrazol-3-yl)methyl; (1-(methylsulfonyl)piperidin-3-yl)methyl; (1-acetylpiperidin-3-yl)methyl; (1-acetylpyrrolidin-2-yl)methyl; (1H-imidazol-2-yl)methyl; (1H-pyrazol-3-yl)methyl; (1-methyl-1H-pyrazol-3-yl)methyl; (1-methyl-1H-pyrazol-5-yl)methyl; (2-(aminocarbonyl)ethylamino)carbonylmethyl; (2-(aminomethyl)pyridin-3-yl)methyl; (2-(carboxy)ethylamino)carbonylmethyl; (2-(dimethylamino)ethylamino)carbonylmethyl; (2-(hydroxy)ethylamino)carbonylmethyl; (2-(methylamino)ethylamino)carbonylmethyl; (2-(N-methyl-N-(t-butoxycarbonyl)-amino)ethylamino)carbonylmethyl; (2-oxopiperidin-3-yl)methyl; (3-(dimethylamino)propylamino)carbonylmethyl; (3-(hydroxy)ethylamino)carbonylmethyl; (3-(t-butoxycarbonylamino)propylamino)carbonylmethyl; (4-(aminomethyl)pyridin-2-yl)methyl; (5-(aminomethyl)pyridin-2-yl)methyl; (6-((1,3-dioxoisoindolin-2-yl)methyl)pyridin-2-yl)methyl; (6-(2-aminoethylamino)pyridin-2-yl)methyl; (6-(3-aminopropylamino)pyridin-2-yl)methyl; (6-(aminomethyl)pyridin-2-yl)methyl; (6-(hydroxymethyl)pyridin-2-yl)methyl; (6-bromopyridin-2-yl)methyl; (methylsulfonamido)carbonylmethyl; (pyridin-2-yl)ethylamino; 1-(2-(tert-butoxycarbonylamino)ethyl)-1H-pyrazol-3-ylmethyl; 1-(2-(tert-butoxycarbonylamino)ethyl)-1H-pyrazol-5-ylmethyl; 1-(aminocarbonyl)-2-(amino)-eth-1-yl; 1-(aminocarbonyl)-3-(amino)-propyl; 1-(aminocarbonyl)-4-(amino)-butyl; 1-(aminocarbonyl)-4-(benzyloxycarbonylamino)-pentyl; 1-(aminocarbonyl)-5-(amino)-pentyl; 1-(aminocarbonyl)eth-1-yl; 1-(carboxy)-2-(amino)-eth-1-yl; 1-(dimethylaminocarbonyl)-2-(amino)-eth-1-yl; 1-(hydroxy)-2-(aminocarbonylmethylamino)eth-1-yl; 1-(hydroxy)-2-(ethoxycarbonylmethylamino)eth-1-yl; 1-(hydroxy)-2-(pyridin-2-ylmethylamino)eth-1-yl; 1-(methoxycarbonyl)-2-(amino)-eth-1-yl; 1-(methoxycarbonyl)-2-(t-butoxycarbonylamino)-eth-1-yl; 1-(methoxycarbonyl)eth-1-yl; 1-(methylaminocarbonyl)-2-(amino)-eth-1-yl (2 occ); 1-(methylaminocarbonyl)eth-1-yl; 1-aminocarbonyl-2-hydroxy-eth-1-yl; 1-methoxycarbonyl-2-hydroxy-eth-1-yl; 2-(2-aminoethoxy)ethyl; 2-(2-aminoethyl)-pyridin-6-ylmethyl; 2-(2-aminoethylamino)ethyl; 2-(3-fluorophenyl)ethyl; 2-(3-methoxycarbonyl)ethyl; 2-(6-(aminomethyl)pyridin-2-yl)ethyl; 2-(acetylamino)ethyl; 2-(amino)ethyl; 2-(aminocarbonyl)-2-(acetylamino)-eth-1-yl; 2-(aminocarbonyl)-2-(amino)-eth-1-yl; 2-(aminocarbonyl)ethyl; 2-(aminomethyl)pyridin-5-ylmethyl; 2-(carboxy)-2-(amino)-eth-1-yl; 2-(dimethylamino)ethyl; 2-(dimethylaminocarbonyl)-2-(amino)-eth-1-yl; 2-(ethoxycarbonyl)ethyl; 2-(methoxycarbonyl)-2-(acetylamino)-eth-1-yl; 2-(methoxycarbonyl)-2-(amino)-eth-1-yl; 2-(methoxycarbonylamino)ethyl; 2-(methylamino)ethyl; 2-(methylaminocarbonyl)-2-(acetylamino)-eth-1-yl; 2-(methylaminocarbonyl)-2-(amino)-eth-1-yl; 2-(methylsulfonamido)ethyl; 2-(methyoxycarbonyl)-2-(amino)-eth-1-yl; 2-(N-(t-butoxycarbonyl)-N-(methyl)-amino)ethyl; 2-(piperazin-1-yl)ethyl; 2-(pyrazin-2-yl)ethyl; 2-(pyridin-2-yl)ethyl; 2-(pyridin-3-yl)ethyl; 2-(t-butoxycarbonylaminomethyl)pyridin-3-ylmethyl; 2-(t-butoxycarbonylaminomethyl)pyridin-6-ylmethyl; 2-(trifluoromethyl)-pyridin-6-ylmethyl; 2-aminopyridin-3-ylmethyl; 2-aminopyridin-5-ylmethyl; 2-chloropyridin-5-ylmethyl; 2-cyanopyridin-5-ylmethyl; 2-hydroxy-3-amino-prop-1-yl; 2-hydroxyethyl; 2-methoxyeth-1-yl; 2-methoxypyridin-3-ylmethyl; 2-methoxypyridin-5-ylmethyl; 2-methylpyridin-3-ylmethyl; 2-methylpyridin-5-ylmethyl; 2-methylpyridin-6-ylmethyl; 3-(2-aminoethyl)cyclohexyl)methyl; 3-(4-methylpiperazin-1-yl)propyl; 3-(amino)-3-(methylaminocarbonyl)prop-1-yl; 3-(aminocarbonyl)propyl; 3-(aminomethyl)benzyl; 3-(aminomethyl)pyridin-2-ylmethyl; 3-(methoxycarbonyl)propyl; 3-(methylaminocarbonyl)propyl; 3-(trifluoromethyl)-pyridin-2-ylmethyl; 3,4-difluorobenzyl; 3-aminomethylpyridin-4-ylmethyl; 3-aminopropyl; 3-carbamoylcyclopentyl; 3-carboxypropyl; 3-hydroxypropyl; 3-methoxypropyl; 4-(aminomethyl)-pyridin-2-ylmethyl; 4-(N,N-dimethylamino)pyridin-3-ylmethyl; 4-(t-butoxycarbonylamino)-morpholinomethyl; 4-aminobutyl; 4-aminomethylpyridin-3-ylmethyl; 4-cyanobenzyl; 4-fluorobenzyl; 4-methylaminopyridin-3-ylmethyl; 4-methylbenzyl; 4-morpholinopyridin-3-ylmethyl; 4-piperazinylpyridin-3-ylmethyl; 5-((bis(dimethylamino)methylamino)methyl)pyridin-3-ylmethyl; 5-(aminomethyl)pyridin-2-ylmethyl; 5-(aminomethyl)pyridin-3-ylmethyl; 5-(hydroxymethyl)pyridin-3-ylmethyl; 5-(t-butoxycarbonylaminomethyl)-pyridin-2-ylmethyl; 5-(trifluoromethyl)-pyridin-2-ylmethyl; 5-aminopentyl; 5-aminopyridin-2-ylmethyl; 6-((bis(dimethylamino)methyleneamino)methyl)pyridin-2-yl)methyl; 6-(4-acetylpiperazin-1-yl)pyridin-3-ylmethyl); 6-(aminomethyl)pyridin-2-yl)methyl; 6-aminohexyl; aminocarbonylmethyl; benzyl; cyclopropylmethyl; dimethylaminocarbonylmethyl; isopropyl; isoxazol-5-ylmethyl; methoxycarbonylmethyl; methyl; methylaminocarbonylmethyl; oxazol-2-ylmethyl; piperidin-4-ylmethyl; prop-2-en-1-yl; pyrazin-2-ylmethyl; pyridin-2-ylmethyl; pyridin-2-ylmethyl-N-oxide; pyridin-3-ylmethyl; pyridin-3-ylmethyl-N-oxide; pyridin-4-ylmethyl; thiophen-2-ylmethyl; and thiophen-3-ylmethyl.

In certain embodiments, $Z^3$ is chosen optionally substituted lower alkyl.

In certain embodiments, $Z^3$ is chosen from optionally substituted methyl, optionally substituted ethyl, and optionally substituted propyl wherein the methyl, ethyl and propyl groups are optionally substituted with one or two groups selected from hydroxy, optionally substituted aryl, optionally substituted heteroaryl, optionally substituted heterocycloalkyl, optionally substituted cycloalkyl, and optionally substituted aryloxy.

In certain embodiments, $Z^3$ is chosen from 2-(3-methylphenyl)ethyl, (tetrahydrofuran-2-yl)methyl, 1-hydroxycyclohexylmethyl, 2-(1,3-dioxolan-2-yl)ethyl, 2-(1H-imidazol-4-yl)ethyl, 2-(1-methyl-1H-imidazol-4-yl)ethyl, 2-(1-methylpiperidin-4-yl)ethyl, 2-(2,3-difluorophenyl)ethyl, 2-(2,5-difluorophenyl)ethyl, 2-(2,6-difluorophenyl)ethyl, 2-(2-chlorophenyl)ethyl, 2-(2-cyanophenyl)ethyl, 2-(2-fluorophenyl)ethyl, 2-(2-hydroxyphenyl)ethyl, 2-(2-methoxyphenyl)ethyl, 2-(2-methylphenyl)ethyl, 2-(2-oxoimidazolidin-1-yl)ethyl, 2-(2-oxopiperidin-1-yl)ethyl, 2-(2-oxopyrrolidin-1-yl)ethyl, 2-(3-(trifluoromethyl)phenyl)ethyl, 2-(3,4-difluorophenyl)ethyl, 2-(3,5-difluorophenyl)ethyl, 2-(3,5-dimethyl-1H-pyrazol-1-yl)ethyl, 2-(3,5-dimethyl-1H-pyrazol-4-yl)ethyl, 2-(3-carbamoylphenyl)ethyl, 2-(3-carboxyphenyl)ethyl, 2-(3-cyanophenyl)ethyl, 2-(3-fluorophenyl)-2-(hydroxy)ethyl, 2-(3-fluorophenyl)ethyl, 2-(3-fluoropyridin-2-yl)ethyl, 2-(3-methoxycarbonylphenyl)ethyl, 2-(3-methoxyphenyl)ethyl, 2-(3-methylphenyl)ethyl, 2-(4-aminophenyl)ethyl, 2-(4-chlorophenyl)ethyl, 2-(4-fluorophenyl)ethyl, 2-(4-hydroxyphenyl)ethyl, 2-(benzo[d][1,3]dioxol-5-yl)ethyl, 2-(furan-2-yl)ethyl, 2-(hydroxy)-2-(phenyl)ethyl, 2-(phenyl)ethyl, 2-(pyridin-2-yl)ethyl, 2-(pyridin-3-yl)ethyl, 2-(thiophen-2-yl)ethyl, 2-cyclohex-1-enylethyl, 2-cyclohexylethyl, 2-morpholinoethyl, 2-phenoxyethyl, 2-phenylprop-1-yl, 3-(1H-imidazol-1-yl)prop-1-yl, 3-phenylpropyl, benzyl, chloro, isopentyl, propyl, pyridin-2-ylmethyl, pyridin-3-ylmethyl, and thiophen-3-ylmethyl.

In certain embodiments, $Z^3$ is chosen from 2-(3-fluorophenyl)ethyl and 2-(pyridin-2-yl)ethyl.

In certain embodiments, $Z^1$ is chosen from cyano, halo, optionally substituted acyl, optionally substituted alkenyl, optionally substituted alkoxycarbonyl, optionally substituted alkyl, optionally substituted amino, optionally substituted aminocarbonyl, and optionally substituted carbamimidoyl.

In certain embodiments, $Z^1$ is chosen from acyl, alkenyl, alkoxycarbonyl, alkyl, amino, aminocarbonyl, and carbamimidoyl, where each group is optionally substituted by one or two groups selected from cyano, halo, hydroxy, formyl, optionally substituted alkyl, optionally substituted alkenyl, optionally substituted alkoxy, carboxyl, optionally substituted alkoxycarbonyl, optionally substituted acyl, optionally substituted aminocarbonyl, optionally substituted heterocycloalkyl, optionally substituted heteroaryl, optionally substituted carbamimidoyl, and optionally substituted sulfonyl.

In certain embodiments, $Z^1$ is chosen from (5-oxo-tetrahydrofuran-2-yl)methylamino; (E)-N'-cyano-N,N-dimethylcarbamimidoyl; (Z)-4-(N-(2-hydroxyethyl)-N,N'-bis(methoxycarbonyl)carbamimidoyl); (Z)-but-2-en-2-yl; 1-ethoxyeth-1-yl; 1-ethoxyvinyl; 2-hydroxyeth-1-ylamino 2-methoxyeth-1-ylamino; 2-methylprop-1-enyl; 3-(methoxycarbonyl)-prop-2-en-2-yl; 3-(N,N-dimethylamino)carbonyl-prop-1-ylamino; 3-aminocarbonyl-prop-1-ylamino; 3-hydroxyprop-1-ylamino; 3-methoxy-prop-1-enyl; 3-methoxyprop-1-ylamino; 3-methoxypropyl; 3-methylbut-2-en-2-yl; 4-((pyridin-3-ylmethyl)aminocarbonyl)butylamino; 4-(N,N-dimethylamino)carbonyl-but-1-ylamino; 4-(N-methylamino)carbonyl-but-1-ylamino; 4-aminocarbonyl-but-1-ylamino; acetyl; aminocarbonyl; carbamimidoyl; chloro; cyano; dimethylamino; ethoxycarbonyl; hydrogen; methoxycarbonyl; methylamino; N-(2-hydroxyethyl)-N-(acetyl)-amino; N-(2-hydroxyethyl)-N-(methyl)-amino; N-(2-hydroxyprop-1-yl)-N-(methyl)-amino; N-(methyl)-aminocarbonyl; N-(pyridin-2-ylmethyl)amino; N-(pyridin-3-ylmethyl)amino; N-(pyridin-4-ylmethyl)amino; N,N-dimethylcarbamimidoyl; N-cyanocarbamimidoyl; N-methyl-N-acetylamino; and prop-1-enyl.

In certain embodiments, $R^1$ is chosen from hydrogen and optionally substituted lower alkyl. In certain embodiments, $R^1$ is chosen from hydrogen and lower alkyl. In certain embodiments, $R^1$ is chosen from hydrogen and methyl. In certain embodiments, $R^1$ is hydrogen.

In certain embodiments, the compound of Formula I is chosen from

| Compound | Chemical Name |
|---|---|
| 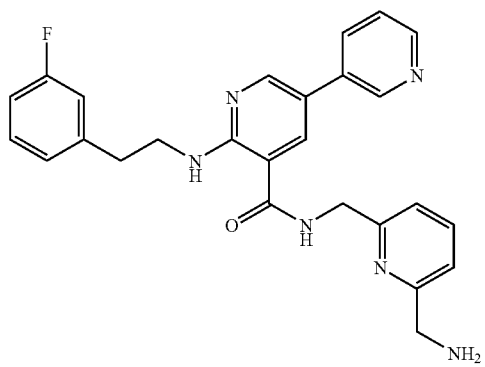<br>Compound 0 | N-{[6-(aminomethyl)(2-pyridyl)]methyl}(2-{[2-(3-fluorophenyl)ethyl]amino}-5-(3-pyridyl)(3-pyridyl))carboxamide |
| 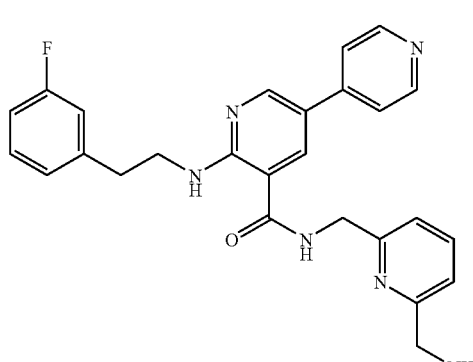<br>Compound 1 | N-{[6-(aminomethyl)(2-pyridyl)]methyl}2-{[2-(3-fluorophenyl)ethyl]amino}-5-(4-pyridyl)(3-pyridyl))carboxamide |

-continued

| Compound | Chemical Name |
|---|---|
| 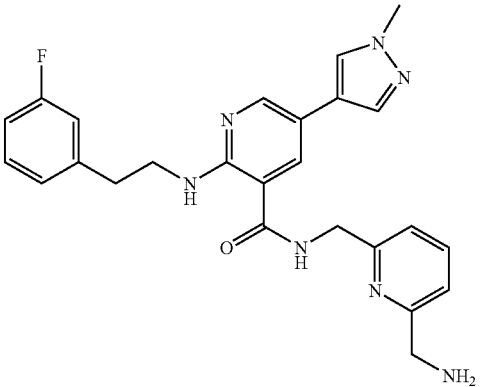<br>Compound 2 | N-{[6-(aminomethyl)(2-pyridyl)]methyl}(2-{[2-(3-fluorophenyl)ethyl]amino}-5-(1-methylpyrazol-4-yl)(3-pyridyl))carboxamide |
| 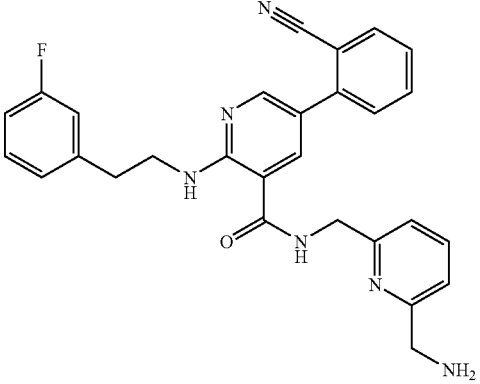<br>Compound 3 | N-{[6-(aminomethyl)(2-pyridyl)]methyl}(5-(2-cyanophenyl)-2-{[2-(3-fluorophenyl)ethyl]amino}(3-pyridyl))carboxamide |
| 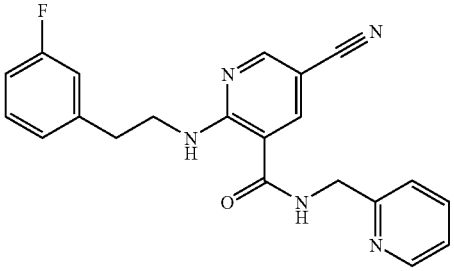<br>Compound 4 | (5-cyano-2-{[2-(3-fluorophenyl)ethyl]amino}(3-pyridyl))-N-(2-pyridylmethyl)carboxamide |
| 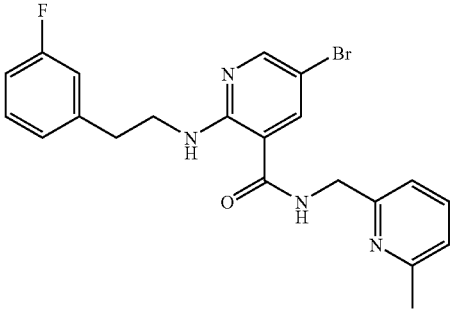<br>Compound 5 | (5-bromo-2-{[2-(3-fluorophenyl)ethyl]amino}(3-pyridyl))-N-[(6-methyl(2-pyridyl))methyl]carboxamide |

-continued

| Compound | Chemical Name |
|---|---|
| Compound 6 | (5-bromo-6-chloro-2-{[2-(3-fluorophenyl)ethyl]amino}(3-pyridyl))-N-(2-pyridylmethyl)carboxamide |
| Compound 7 | 5-bromo-2-{[2-(3-fluorophenyl)ethyl]amino}pyridine-3-carboxylic acid |
| Compound 8 | methyl 5-cyano-2-{[2-(3-fluorophenyl)ethyl]amino}pyridine-3-carboxylate |
| Compound 9 | N-({6-[(1,3-dioxobenzo[c]azolin-2-yl)methyl](2-pyridyl)}methyl)(5-bromo-2-{[2-(3-fluorophenyl)ethyl]amino}(3-pyridyl))carboxamide |
| Compound 10 | (5-bromo-2-{[2-(3-fluorophenyl)ethyl]amino}(3-pyridyl))-N-(2-pyridylmethyl)carboxamide |

| Compound | Chemical Name |
|---|---|
| 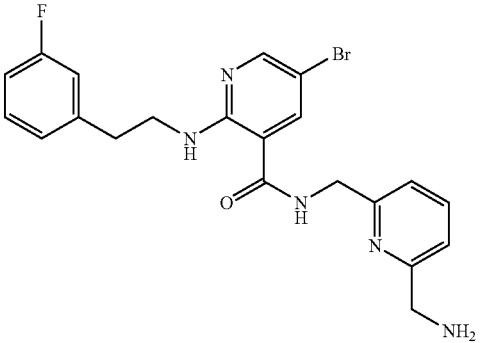<br>Compound 11 | N-{[6-(aminomethyl)(2-pyridyl)]methyl}(5-bromo-2-{[2-(3-fluorophenyl)ethyl]amino}(3-pyridyl))carboxamide |
| 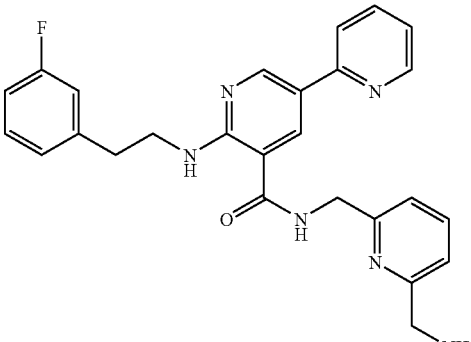<br>Compound 12 | N-{[6-(aminomethyl)(2-pyridyl)]methyl}(2-{[2-(3-fluorophenyl)ethyl]amino}-5-(2-pyridyl)(3-pyridyl))carboxamide |
| 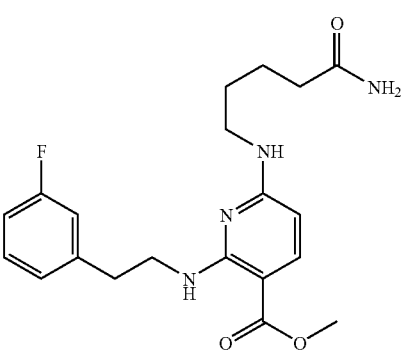<br>Compound 13 | methyl 6-[(4-carbamoylbutyl)amino]-2-{[2-(3-fluorophenyl)ethyl]amino}pyridine-3-carboxylate |
| 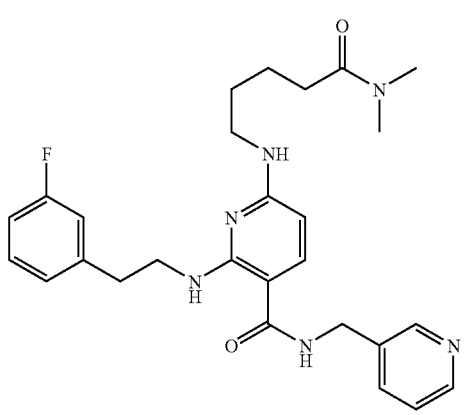<br>Compound 14 | 5-[(6-{[2-(3-fluorophenyl)ethyl]amino}-5-[N-(3-pyridylmethyl)carbamoyl](2-pyridyl))amino]-N,N-dimethylpentanamide |

| Compound | Chemical Name |
|---|---|
| 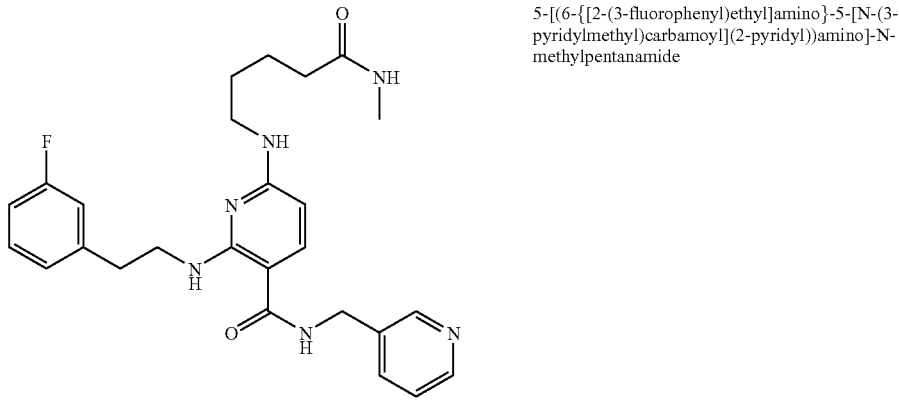<br>Compound 15 | 5-[(6-{[2-(3-fluorophenyl)ethyl]amino}-5-[N-(3-pyridylmethyl)carbamoyl](2-pyridyl))amino]-N-methylpentanamide |
| 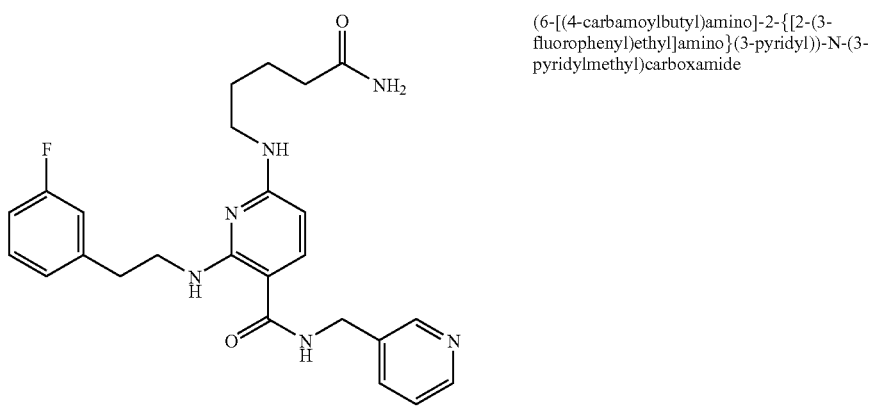<br>Compound 16 | (6-[(4-carbamoylbutyl)amino]-2-{[2-(3-fluorophenyl)ethyl]amino}(3-pyridyl))-N-(3-pyridylmethyl)carboxamide |
| 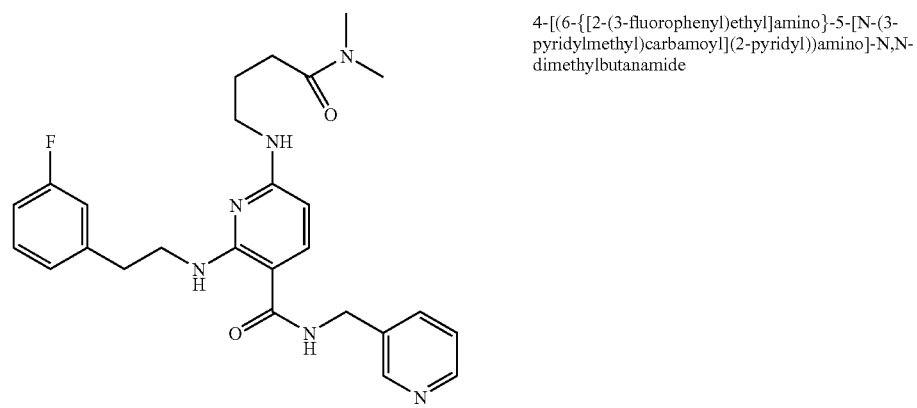<br>Compound 17 | 4-[(6-{[2-(3-fluorophenyl)ethyl]amino}-5-[N-(3-pyridylmethyl)carbamoyl](2-pyridyl))amino]-N,N-dimethylbutanamide |

-continued

| Compound | Chemical Name |
|---|---|
| 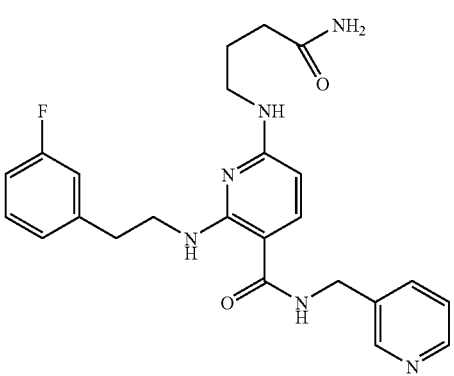  Compound 18 | (6-[(3-carbamoylpropyl)amino]-2-{[2-(3-fluorophenyl)ethyl]amino}(3-pyridyl))-N-(3-pyridylmethyl)carboxamide |
| 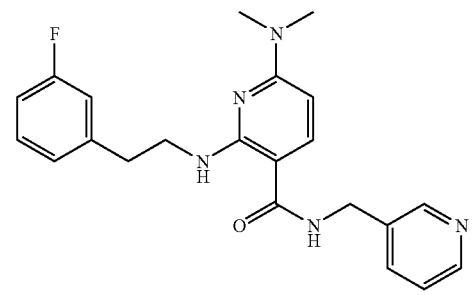  Compound 19 | (6-(dimethylamino)-2-{[2-(3-fluorophenyl)ethyl]amino}(3-pyridyl))-N-(3-pyridylmethyl)carboxamide |
| 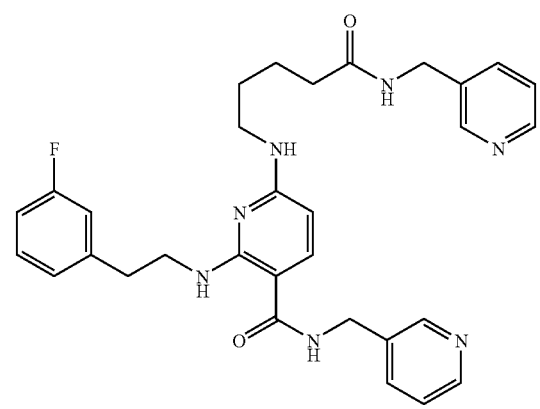  Compound 20 | 5-[(6-{[2-(3-fluorophenyl)ethyl]amino}-5-[N-(3-pyridylmethyl)carbamoyl](2-pyridyl))amino]-N-(3-pyridylmethyl)pentanamide |
| 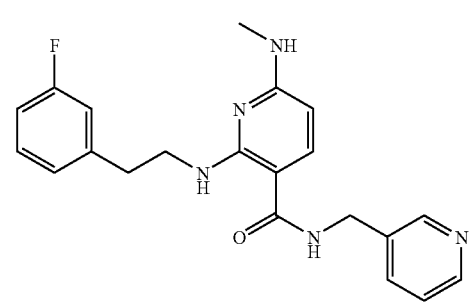  Compound 21 | (2-{[2-(3-fluorophenyl)ethyl]amino}-6-(methylamino)(3-pyridyl))-N-(3-pyridylmethyl)carboxamide |

-continued

| Compound | Chemical Name |
|---|---|
| 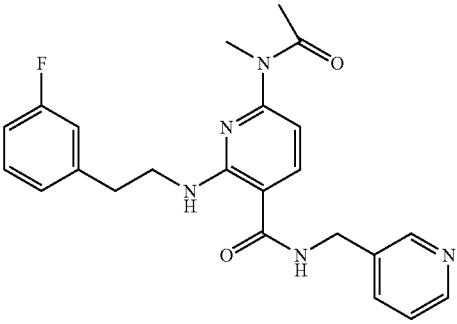<br>Compound 22 | N-(6-{[2-(3-fluorophenyl)ethyl]amino}-5-[N-(3-pyridylmethyl)carbamoyl](2-pyridyl))-N-methylacetamide |
| 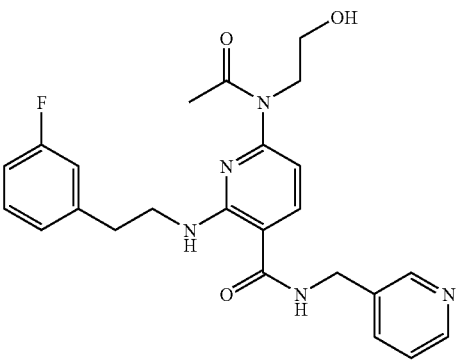<br>Compound 23 | N-(6-{[2-(3-fluorophenyl)ethyl]amino}-5-[N-(3-pyridylmethyl)carbamoyl](2-pyridyl))-N-(2-hydroxyethyl)acetamide |
| 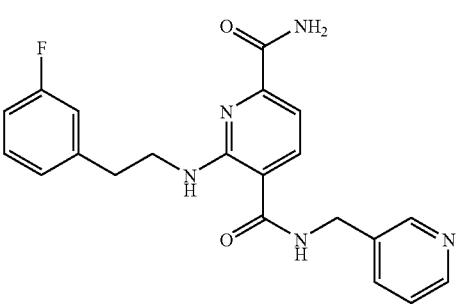<br>Compound 24 | 6-{[2-(3-fluorophenyl)ethyl]amino}-5-[N-(3-pyridylmethyl)carbamoyl]pyridine-2-carboxamide |
| 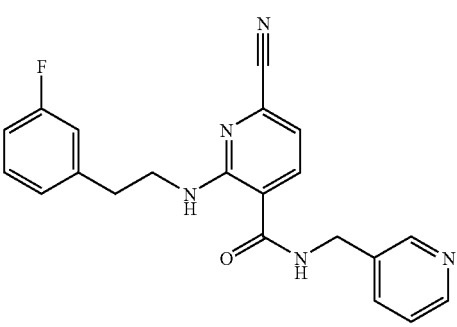<br>Compound 25 | (6-cyano-2-{[2-(3-fluorophenyl)ethyl]amino}(3-pyridyl))-N-(3-pyridylmethyl)carboxamide |

| Compound | Chemical Name |
|---|---|
| Compound 26 | (2-{[2-(3-fluorophenyl)ethyl]amino}-6-[(3-pyridylmethyl)amino](3-pyridyl))-N-(3-pyridylmethyl)carboxamide |
| Compound 27 | (6-[(cyanoamino)iminomethyl]-2-{[2-(3-fluorophenyl)ethyl]amino}(3-pyridyl))-N-(3-pyridylmethyl)carboxamide |
| Compound 28 | (6-((1Z)-1-methylprop-1-enyl)-2-{[2-(3-fluorophenyl)ethyl]amino}(3-pyridyl))-N-(3-pyridylmethyl)carboxamide |
| Compound 29 | (2-{[2-(3-fluorophenyl)ethyl]amino}-6-(N-methylcarbamoyl)(3-pyridyl))-N-(3-pyridylmethyl)carboxamide |

| Compound | Chemical Name |
|---|---|
| 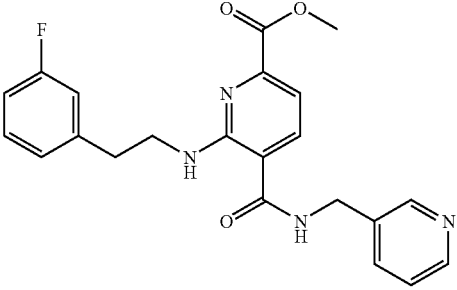<br>Compound 30 | methyl 6-{[2-(3-fluorophenyl)ethyl]amino}-5-[N-(3-pyridylmethyl)carbamoyl]pyridine-2-carboxylate |
| 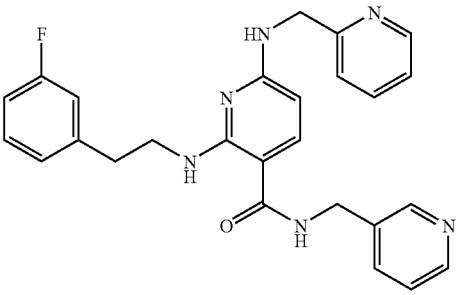<br>Compound 31 | (2-{[2-(3-fluorophenyl)ethyl]amino}-6-[(2-pyridylmethyl)amino](3-pyridyl))-N-(3-pyridylmethyl)carboxamide |
| 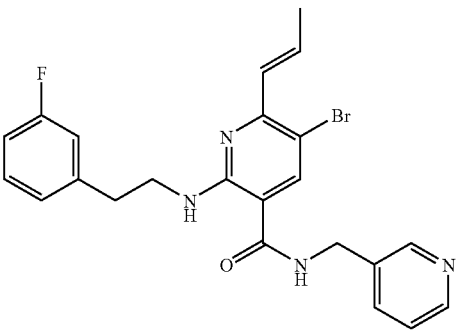<br>Compound 32 | (6-((1E)prop-1-enyl)-5-bromo-2-{[2-(3-fluorophenyl)ethyl]amino}(3-pyridyl))-N-(3-pyridylmethyl)carboxamide |
| 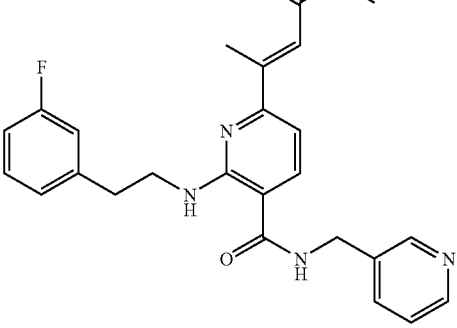<br>Compound 33 | methyl (2E)-3-(6-{[2-(3-fluorophenyl)ethyl]amino}-5-[N-(3-pyridylmethyl)carbamoyl](2-pyridyl))but-2-enoate |

| Compound | Chemical Name |
|---|---|
| Compound 34 | (2-{[2-(3-fluorophenyl)ethyl]amino}-6-[(4-pyridylmethyl)amino](3-pyridyl))-N-(3-pyridylmethyl)carboxamide |
| Compound 35 | ethyl 6-{[2-(3-fluorophenyl)ethyl]amino}-5-[N-(3-pyridylmethyl)carbamoyl]pyridine-2-carboxylate |
| Compound 36 | (6-((1E)prop-1-enyl)-2-{[2-(3-fluorophenyl)ethyl]amino}(3-pyridyl))-N-(3-pyridylmethyl)carboxamide |
| Compound 37 | (6-((1E)prop-1-enyl)-5-cyano-2-{[2-(3-fluorophenyl)ethyl]amino}(3-pyridyl))-N-(3-pyridylmethyl)carboxamide |

| Compound | Chemical Name |
|---|---|
| 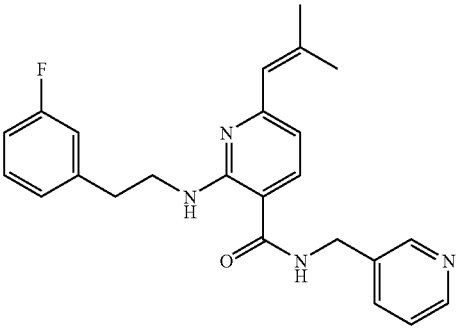<br>Compound 38 | (2-{[2-(3-fluorophenyl)ethyl]amino}-6-(2-methylprop-1-enyl)(3-pyridyl))-N-(3-pyridylmethyl)carboxamide |
| 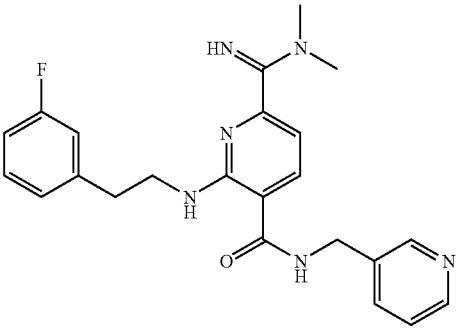<br>Compound 39 | (6-[(dimethylamino)iminomethyl]-2-{[2-(3-fluorophenyl)ethyl]amino}(3-pyridyl))-N-(3-pyridylmethyl)carboxamide |
| 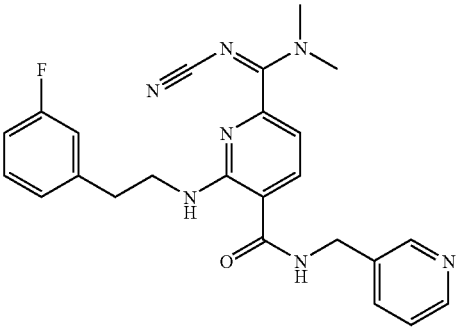<br>Compound 40 | (6-[(1E)-1-(dimethylamino)-2-cyano-2-azavinyl]-2-{[2-(3-fluorophenyl)ethyl]amino}(3-pyridyl))-N-(3-pyridylmethyl)carboxamide |
| 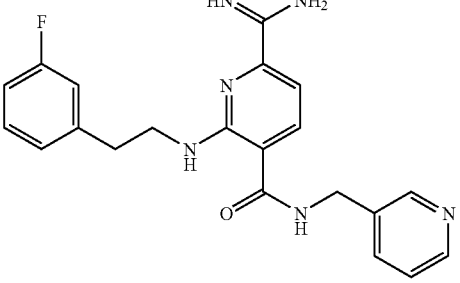<br>Compound 41 | 6-{[2-(3-fluorophenyl)ethyl]amino}-5-[N-(3-pyridylmethyl)carbamoyl]pyridine-2-carboxamidine |

| Compound | Chemical Name |
|---|---|
| Compound 42 | 2-[(2-{[2-(3-fluorophenyl)ethyl]amino}-5-phenyl(3-pyridyl))carbonylamino]-N-methylacetamide |
| (boc) | (6-((1E)prop-1-enyl)-2-{[2-(3-fluorophenyl)ethyl]amino}(3-pyridyl))-N-{[2-(aminomethyl)(3-pyridyl)]methyl}carboxamide |
| Compound 43 | 2-[(5-(2-cyanophenyl)-2-{[2-(3-fluorophenyl)ethyl]amino}(3-pyridyl))carbonylamino]-N-methylacetamide |
| Compound 44 | (6-((1E)-3-methoxyprop-1-enyl)-2-{[2-(3-fluorophenyl)ethyl]amino}(3-pyridyl))-N-(3-pyridylmethyl)carboxamide |

| Compound | Chemical Name |
|---|---|
| Compound 45 | (6-(ethoxyethyl)-2-{[2-(3-fluorophenyl)ethyl]amino}(3-pyridyl))-N-(3-pyridylmethyl)carboxamide |
| Compound 46 | (6-acetyl-2-{[2-(3-fluorophenyl)ethyl]amino}(3-pyridyl))-N-(3-pyridylmethyl)carboxamide |
| Compound 47 | (6-((1E)prop-1-enyl)-5-fluoro-2-{[2-(3-fluorophenyl)ethyl]amino}(3-pyridyl))-N-{[2-(aminomethyl)(3-pyridyl)]methyl}carboxamide |
| Compound 48 | (6-((1E)prop-1-enyl)-5-fluoro-2-{[2-(3-fluorophenyl)ethyl]amino}(3-pyridyl))-N-[(2-{[(tert-butoxy)carbonylamino]methyl}(3-pyridyl)methyl]carboxamide |

| Compound | Chemical Name |
|---|---|
| Compound 49 | N-{[2-(aminomethyl)(3-pyridyl)]methyl}(5-fluoro-2-{[2-(3-fluorophenyl)ethyl]amino}(3-pyridyl))carboxamide |
| Compound 50 | (2-{[2-(3-fluorophenyl)ethyl]amino}(3-pyridyl))-N-(3-pyridylmethyl)carboxamide |
| Compound 51 | (6-(1,2-dimethylprop-1-enyl)-2-{[2-(3-fluorophenyl)ethyl]amino}(3-pyridyl))-N-(3-pyridylmethyl)carboxamide |
| Compound 52 | (2-{[2-(3-fluorophenyl)ethyl]amino}-6-(3-methoxypropyl)(3-pyridyl))-N-(3-pyridylmethyl)carboxamide |

-continued

| Compound | Chemical Name |
|---|---|
| Compound 53 | (6-(1-ethoxyvinyl)-2-{[2-(3-fluorophenyl)ethyl]amino}(3-pyridyl))-N-(3-pyridylmethyl)carboxamide |
| Compound 54 | (2-{[2-(3-fluorophenyl)ethyl]amino}-6-[(2-hydroxyethyl)amino](3-pyridyl))-N-(3-pyridylmethyl)carboxamide |
| Compound 55 | (2-{[2-(3-fluorophenyl)ethyl]amino}-6-[(2-hydroxyethyl)methylamino](3-pyridyl))-N-(3-pyridylmethyl)carboxamide |

| Compound | Chemical Name |
|---|---|
| 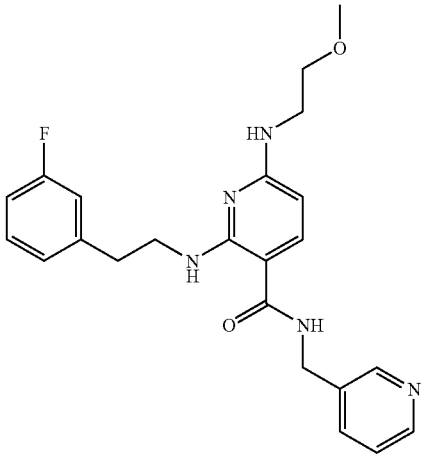
Compound 56 | (2-{[2-(3-fluorophenyl)ethyl]amino}-6-[(2-methoxyethyl)amino](3-pyridyl))-N-(3-pyridylmethyl)carboxamide |
| 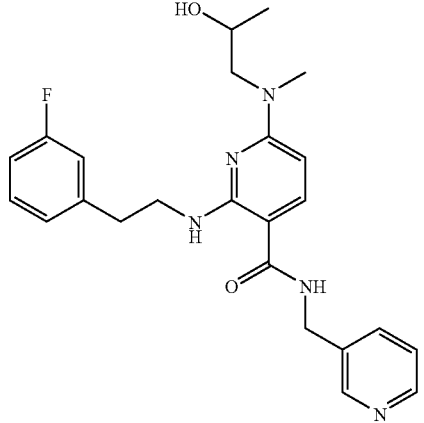
Compound 57 | (2-{[2-(3-fluorophenyl)ethyl]amino}-6-[(2-hydroxypropyl)methylamino](3-pyridyl))-N-(3-pyridylmethyl)carboxamide |
| 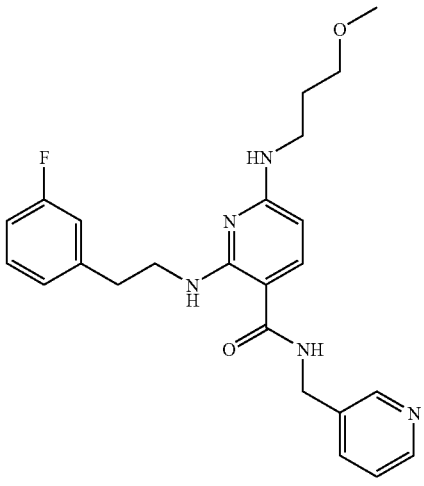
Compound 58 | (2-{[2-(3-fluorophenyl)ethyl]amino}-6-[(3-methoxypropyl)amino](3-pyridyl))-N-(3-pyridylmethyl)carboxamide |

| Compound | Chemical Name |
|---|---|
| (structure) | (2-{[2-(3-fluorophenyl)ethyl]amino}-6-[(3-hydroxypropyl)amino](3-pyridyl))-N-(3-pyridylmethyl)carboxamide |

The compounds described herein can be synthesized utilizing techniques well known in the art from commercially available starting materials and reagents. For example, the compounds described herein can be prepared as shown below.

Unless specified to the contrary, for each gram of the limiting reagent, one cc (or mL) of solvent constitutes a volume equivalent.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures are provided in the Example. However, other equivalent separation or isolation procedures can, of course, also be used.

When desired, the (R) and (S) isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that when the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts and/or solvents, or by converting one enantiomer to the other by asymmetric transformation.

The chemical entities described herein may be useful in a variety of applications involving smooth muscle cells and/or non-muscle cells. In certain embodiments, the chemical entities may be used to inhibit smooth muscle myosin. The chemical entities may be useful to bind to, and/or inhibit the activity of, smooth muscle myosin. In certain embodiments, the smooth muscle myosin is human, although the chemical entities may be used to bind to or inhibit the activity of smooth muscle myosin from other organisms, such as other mammals.

In certain embodiments, the chemical entities may be used to inhibit non-muscle myosin. The chemical entities may be useful to bind to, and/or inhibit the activity of, non-muscle myosin. In certain embodiments, the non-muscle myosin is human, although the chemical entities may be used to bind to or inhibit the activity of non-muscle myosin from other organisms, such as other mammals.

The chemical entities described herein may be used to treat disease states associated with smooth muscle and/or non-muscle myosin. Such disease states which can be treated by the chemical entities described herein include, but are not limited to, hypertension, asthma, incontinence, chronic obstructive pulmonary disorder, pre-term labor, and the like. It is appreciated that in some cases the cells may not be in an abnormal state and still require treatment. Thus, in certain embodiments, the chemical entities described herein can be applied to cells or administered to individuals afflicted or subject to impending affliction with any one of these disorders or states.

More specifically, the chemical entities described herein may be useful for the treatment of diseases or symptoms related to abnormal increased muscle tone or excessive contraction, or spasm of vascular smooth muscle in systemic, coronary, pulmonary circulation, and micro-circulatory smooth muscle as well, such as systemic hypertension, malignant hypertension, hypertension crisis, symptomatic hypertension, pulmonary hypertension, pulmonary infarction, angina pectoris, cardiac infarction, micro-circulation malfunction under shock condition, and infarction occurred in other location or organs of the human or animal body. Other diseases or symptoms that can be treated with the chemical entities described herein include:

spasm of gastro-intestine smooth muscle, including sphincters, such as gastric spasm, pylorospasm, and spasms of biliary tract, pancreatic tract, urinary tract, caused by inflammation, stimulation of stones or parasites;

spasm of other visceral organs such as uterus, Fallopian tube, and so on;

spasm of trachea-bronchial tree smooth muscle, diaphragm muscle, such as various asthma, breathlessness, dyspnea, diaphragmatic convulsion, and so on;

spasm of alimentary canal smooth muscle, including stomach, intestine and colons, biliary and pancreatic duct etc.; and spasm of urinary tract smooth muscle.

In addition, the chemical entities described herein can be used for control, management and manipulation of labor during pregnancy. The method is particularly useful for inhibition of spontaneous preterm labor which would, if untreated, result in premature delivery or abortion and for inhibition of surgically induced labor during transuterine fetal surgery. The method is also useful for inducing the labor in overterm pregnancies where the labor does not occur on term and when it is necessary to induce labor in order to assure the normal delivery.

Further, the chemical entities described herein can be used for the treatment of "airway wall remodeling", which is a condition associated with diseases or conditions characterized by airway wall thickening and air obstruction, which may, for example occur in the small airways of patients with certain respiratory disease conditions, such as, chronic obstructive pulmonary disease (COPD).

Such disease states which can be treated by the chemical entities, compositions and methods provided herein also include, but are not limited to glaucoma and other ocular indications. More specifically, chemical entities described herein may be useful for the treatment of diseases or symptoms related to glaucoma, including increased intraocular pressure, reduced flow of intraocular aqueous humor, and optical nerve damage. Other diseases or symptoms that can be treated with the chemical entities, compositions, and methods described herein including intraocular hypertenstion.

ATP hydrolysis is employed by myosin to produce force. An increase in ATP hydrolysis would correspond to an increase in the force or velocity of muscle contraction. In the presence of actin, myosin ATPase activity is stimulated more than 100-fold. Thus, the measurement of ATP hydrolysis not only measures myosin enzymatic activity but also its interaction with the actin filament. Assays for such activity may employ smooth muscle myosin from a human source, although myosin from other organisms can also be used. Systems that model the regulatory role of calcium in myosin binding may also be used.

The in vitro rate of ATP hydrolysis correlates to smooth muscle myosin potentiating activity, which can be determined by monitoring the production of either ADP or phosphate, for example as described in U.S. Pat. No. 6,410,254. ADP production can also be monitored by coupling the ADP production to NADH oxidation (using, for example, the enzymes pyruvate kinase and lactate dehydrogenase) and monitoring the NADH level, by example, either by absorbance or fluorescence (Greengard, P., *Nature* 178 (Part 4534): 632-634 (1956); *Mol Pharmacol* 1970 January; 6(1):31-40). Phosphate production can be monitored using purine nucleoside phosphorylase to couple phosphate production to the cleavage of a purine analog, which results in either a change in absorbance (*Proc Natl Acad Sci USA* 1992 June 1; 89(11): 4884-7) or fluorescence (*Biochem J* 1990 March 1; 266(2): 611-4). While a single measurement is employed, multiple measurements of the same sample at different times in order may be used to determine the absolute rate of the protein activity; such measurements have higher specificity particularly in the presence of test compounds that have similar absorbance or fluorescence properties with those of the enzymatic readout.

Test compounds may be assayed in a highly parallel fashion using multiwell plates by placing the compounds either individually in wells or testing them in mixtures. Assay components including the target protein complex, coupling enzymes and substrates, and ATP may then be added to the wells and the absorbance or fluorescence of each well of the plate can be measured with a plate reader.

One method uses a 384 well plate format and a 25 µL reaction volume. A pyruvate kinase/lactate dehydrogenase coupled enzyme system (Huang T G and Hackney DD. (1994) J Biol Chem 269(23):16493-16501) is used to measure the rate of ATP hydrolysis in each well. As will be appreciated by those of skill in the art, the assay components are added in buffers and reagents. Since the methods outlined herein allow kinetic measurements, incubation periods may be optimized to give adequate detection signals over the background. The assay is performed in real time to give the kinetics of ATP hydrolysis to increase the signal-to-noise ratio of the assay.

Selectivity for smooth muscle myosin may be determined by substituting other myosins in one or more of the above-described assays and comparing the results obtained against those obtained using the cardiac equivalents.

Chemical entities identified by the methods described herein as smooth muscle myosin modulators may be further tested in an efficacy screen, such as a screen using strips of permeabilized smooth muscle from, e.g., chicken gizzard. Calcium-sensitive smooth muscle strips are prepared by dissecting chicken gizzard tissue, followed by treatment with 1% Triton X-100 to make the strips permeable to exogenous compounds (Barsotti, R J, et al., Am J Physiol. 1987 May; 252(5 Pt 1):C543-54). These strips can be stored in 50% glycerol for several weeks at −20° C., allowing multiple experiments to be performed with each batch of muscle strips. Experiments are performed using a solution of 20 mM imidazole pH 7.0, 5.5 mM ATP, 7 mM $MgCl_2$, 55 mM KCl, 1 µM Calmodulin, and 10 mM EGTA. Free calcium will be controlled by addition of various amounts of $CaCl_2$, according to the calculations of MAXChelator (Patton, et al. Cell Calcium. 35/5 pp. 427-431, 2004). An isometric muscle fiber apparatus is used to measure isometric tension, for example using an Aurora Scientific 400A transducer with National Instruments PCI-MIO-16E-4, 16 channels, 12 bit A/D board for data acquisition. The chemically skinned gizzard fibers are relaxed when bathed in low calcium solutions (pCa 8), but develop isometric tension when the free calcium of the bathing solution is increased to pCa 5. These fibers can be repeatedly contracted and relaxed by switching between high and low calcium bathing solutions.

Compounds are first tested for their ability to prevent contraction of gizzard strips, by preincubating relaxed fibers with a compound, followed by transfer to high calcium solution containing the compound. Next, compounds are tested for their ability to cause relaxation of contracting fibers by adding the compound to fibers already incubating in high calcium solution. Washout experiments are performed to ensure that the inhibitory effects are reversible, so that the compounds do not cause denaturation or other irreparable damage to the smooth muscle myosin.

The chemical entities are administered at a therapeutically effective dosage, e.g., a dosage sufficient to provide treatment of the disease states previously described. Generally, a daily dose is from about 0.05 to about 100 mg/kg of body weight, such as from about 0.10 to about 10 mg/kg of body weight or from about 0.15 to about 1 mg/kg of body weight. Thus, for administration to a 70 kg person, the dosage range is from about 3.5 to about 7000 mg per day, such as from about 7 to about 700 mg per day or from about 10 to about 100 mg per day. The amount of active chemical entity administered will, of course, be dependent on the subject and disease state being treated, the severity of the affliction, the manner and schedule of administration and the judgment of the prescribing physician; for example, a dose range for oral administration may be from about 70 to about 700 mg per day, whereas for intravenous administration the dose range may be from about 700 to about 7000 mg per day. The active agents may be selected for longer or shorter plasma half-lives, respectively.

Administration of the chemical entities described herein including pharmaceutically acceptable salts thereof can be via any of the accepted modes of administration for agents that serve similar utilities including, but not limited to, orally, subcutaneously, intravenously, intranasally, topically, transdermally, sublingually, intramucosally, intraperitoneally, intramuscularly, intrapulmonarilly, vaginally, rectally, and intraocularly (including intraocular injection). Oral, topical, parenteral, and intraocular administration are customary in treating many of the indications recited herein.

Pharmaceutically acceptable compositions include solid, semi-solid, liquid and aerosol dosage forms, such as, e.g., tablets, capsules, powders, liquids, suspensions, suppositories, aerosols, and the like. The chemical entities can also be administered in sustained- or controlled-release dosage forms, including depot injections, osmotic pumps, pills, transdermal (including electrotransport) patches, drops and the like, for prolonged and/or timed, pulsed administration at a predetermined rate. The compositions may be provided in unit dosage forms suitable for single administration of a precise dose.

The chemical entities may be administered either alone or in combination with a conventional pharmaceutical carrier or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition may also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate. Generally, depending on the intended mode of administration, the pharmaceutical composition may contain from about 0.005% to about 95%, for example, from about 0.5% to about 50%, by weight of at least one chemical entity described herein. Actual methods of preparing such dosage forms are known or will be apparent, to those skilled in this art; for example, see *Remington's Pharmaceutical Sciences*, Mack Publishing Company, Easton, Pa. Pharmaceutical compositions are also referred to as pharmaceutical formulations.

In addition, the chemical entities may be co-administered with, and the pharmaceutical compositions can include, other medicinal agents, pharmaceutical agents, adjuvants, and the like.

In certain embodiments, the compositions are in the form of a pill or tablet and contain, along with the active ingredient, one or more of a diluent such as lactose, sucrose, dicalcium phosphate, and the like; a lubricant such as magnesium stearate or the like; and a binder such as starch, gum acacia, polyvinylpyrrolidine, gelatin, cellulose, cellulose derivatives and the like. In another solid dosage form, a powder, marume, solution or suspension (e.g., in propylene carbonate, vegetable oils or triglycerides) may be encapsulated in a gelatin capsule.

Liquid pharmaceutical compositions may, for example, be prepared by dissolving, dispersing, etc. at least one chemical entity and one or more optional pharmaceutical adjuvants in a carrier (e.g., water, saline, aqueous dextrose, glycerol, glycols, ethanol and the like) to form a solution or suspension. Injectables may be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient ranging from about 0.01% to about 10% in solution may be used, and may be higher if the composition is a solid which will be subsequently diluted to the above percentages. In certain embodiments, the composition has from about 0.2% to about 2% of the active agent in solution.

Compositions comprising at least one chemical entity may be administered intraocularly (including intraocular, periocular, and retrobulbar injection and perfusion). When administered intraocularly the sterile composition is typically aqueous. An appropriate buffer system may be added to prevent pH drift under storage conditions. When administered during intraocular surgical procedures, such as retrobulbar or periocular injection and intraocular perfusion or injection, the use of balanced salt irrigating solutions may be necessary. When used in a multidose form, preservatives may be required to prevent microbial contamination during use.

Compositions comprising at least one chemical entity may also be administered topically as eye drops, eye wash, creams, ointments, gels, and sprays. When administered as eye drops or eye wash, the active ingredients are typically dissolved or suspended in suitable carrier, typically a sterile aqueous solvent. An appropriate buffer system may be added to prevent pH drift under storage conditions. When used in a multidose form, preservatives may be required to prevent microbial contamination during use.

Compositions comprising at least one chemical entity may also be administered to the respiratory tract as an aerosol or in a solution for a nebulizer, or as a microfine powder for insufflation, alone or in combination with an inert carrier such as lactose. The particles of the composition typically have diameters of less than 50 microns, for example, less than 10 microns.

Generally, to employ the chemical entities described herein in methods of screening for smooth muscle myosin binding, smooth muscle myosin is bound to a support and at least one chemical entity is added to the assay. Alternatively, the chemical entity may be bound to the support and the smooth muscle myosin added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.), and the like. See, e.g., U.S. Pat. No. 6,495,337.

EXAMPLES

The following examples serve to more fully describe the manner of using the invention. These examples are presented for illustrative purposes and should not serve to limit the true scope of the invention.

Example I

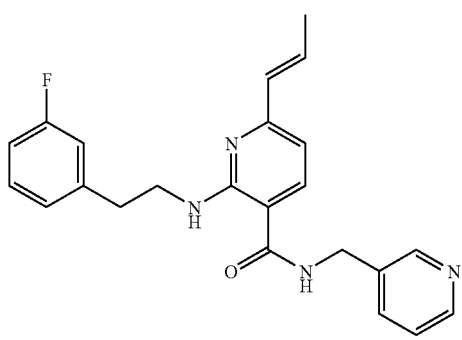

(E)-2-(3-fluorophenethylamino)-6-(prop-1-enyl)-N-(pyridin-3-ylmethyl)nicotinamide

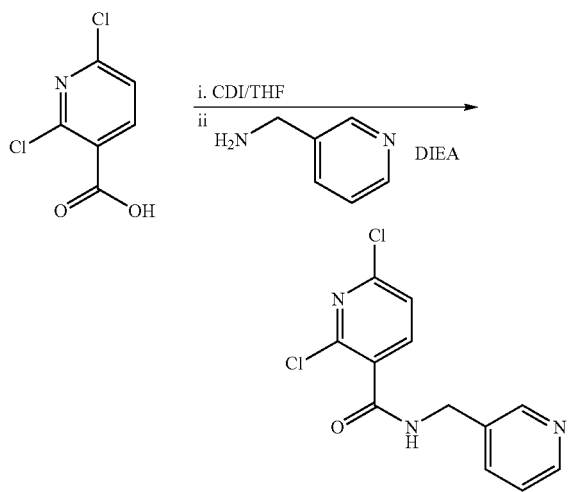

A mixture of acid 2,6-dichloronicotinic acid (19.2 g, 0.1 mol), N,N'-carbonyldiimidazole (CDI, 17.8 g, 0.11 mmol) and THF (1 L) was stirred at 60° C. for 30 min and cooled to room temperature. To the mixture was added 3-aminomethylpyridine (10.2 mL, 0.1 mol) and DIEA (21 mL, 0.12 mol). The reaction mixture was stirred at room temperature for 4 hrs, and diluted with EtOAc. The organic layer was washed with H$_2$O, brine, dried over Na$_2$SO$_4$. Concentration of the organic solution gave the 2,6-dichloro-N-(pyridin-3-ylmethyl)nicotinamide (20.5 g, 73%). LRMS (M+H$^+$) m/z 282.0; (M+2+H$^+$) m/z 283.9.

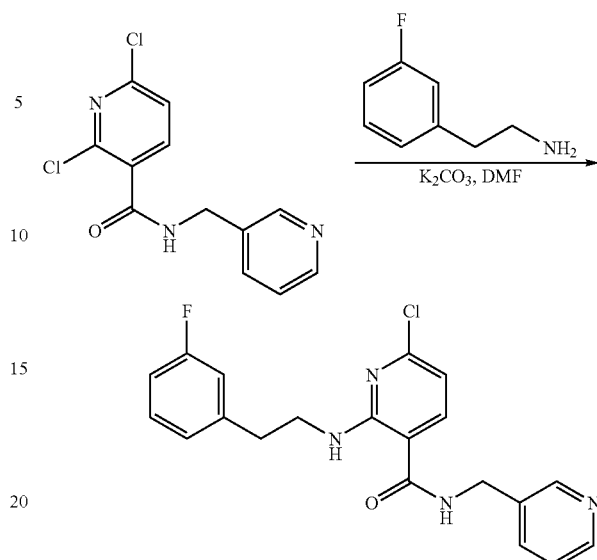

A mixture of chloride 2,6-dichloro-N-(pyridin-3-ylmethyl)nicotinamide (20.4 g, 72.3 mmol), 3-fluorophenethyl amine (11.1 g, 79.5 mmol), K$_2$CO$_3$ (20 g 145 mmol) and DMF (200 mL) was stirred at 10° C. for 10 hours. The mixture was diluted with ethyl acetate (2×300 mL) and washed with saturated ammonium chloride, sodium bicarbonate and brine. The organic layers were combined, dried (MgSO$_4$) and concentrated. The residue was purified by silica gel chromatography to give the desired product 6-chloro-2-(3-fluorophenethylamino)-N-(pyridin-3-ylmethyl)nicotinamide (12.6 g, 46%). LRMS (M+H$^+$) m/z 385.1.

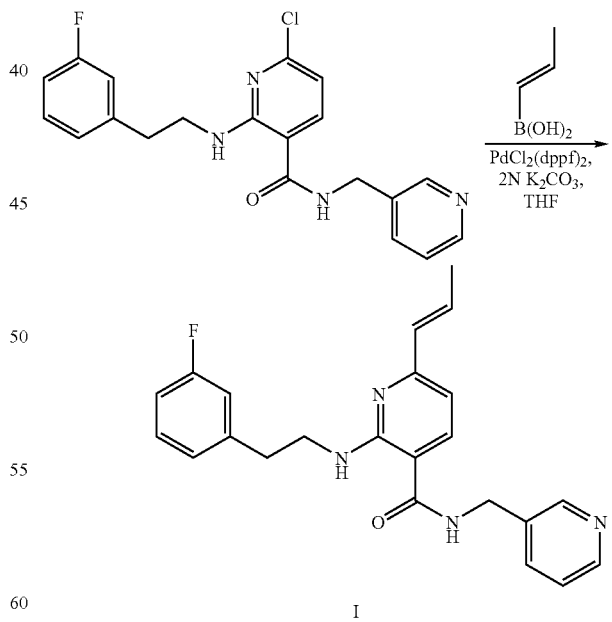

A mixture of chloride 6-chloro-2-(3-fluorophenethylamino)-N-(pyridin-3-ylmethyl)nicotinamide (100 mg, 0.260 mmol), trans-1-propen-1-yl boronic acid (27 mg, 0.312 mmol), PdCl$_2$(dppf)$_2$ (14 mg, 0.026 mmol), 2N K$_2$CO$_3$(0.39 mL, 0.78 mmol) and THF (1.5 mL) was stirred at 125° C. for 30 min. The mixture was filtered through the silica gel pad and washed with EtOAc. The filtrate was concentrated to dryness and purified on RP-HPLC using a mixture of acetonitrile and H₂O to give (E)-2-(3-fluorophenethylamino)-6-(prop-1-enyl)-N-(pyridin-3-ylmethyl)nicotinamide as a pale yellow solid (59 mg, 86%). LRMS (M+H⁺) m/z 391.2.

Example II

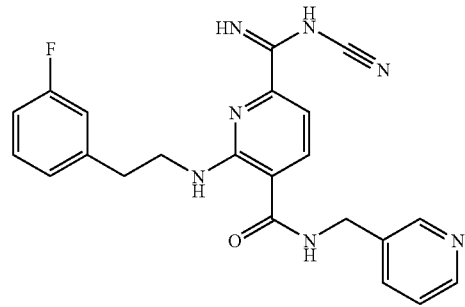

2-(3-fluorophenethylamino)-6-(cyanoimidamide)-N-(pyridine-3-ylmethyl)nicotinamide

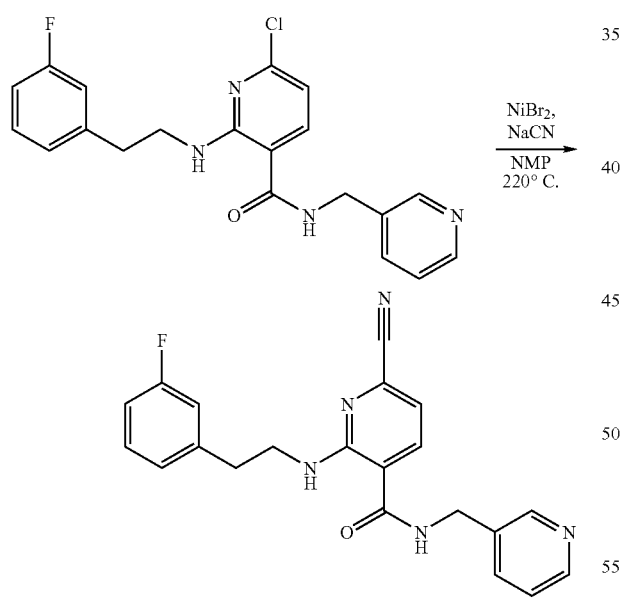

A mixture of 6-chloro-2-(3-fluorophenethylamino)-N-(pyridin-3-ylmethyl)nicotinamide (1.3 g, 3.3 mmol), NiBr₂ (1.1 g, 4.9 mmol), NaCN (0.48 g, 9.8 mmol) and NMP (6 mL) was stirred at 220° C. for 1 hour. The reaction mixture was filtered through Celite with EtOAc. The organics were washed with water, brine, dried (Na₂SO₄) and concentrated to give the nitrile 6-cyano-2-(3-fluorophenethylamino)-N-(pyridin-3-ylmethyl)nicotinamide (0.85 g, 69%). LC/MS (M+H⁺) m/z 376.1.

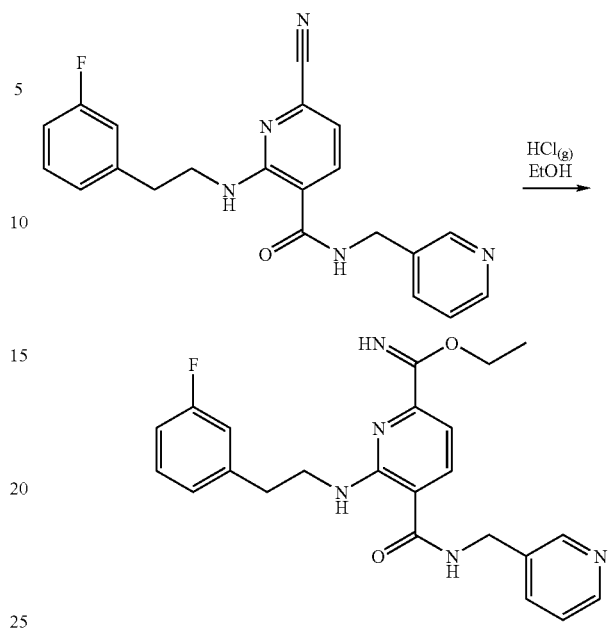

A three neck round bottom flask fixed with a dry ice acetone condenser was charged with the nitrile nitrile 6-cyano-2-(3-fluorophenethylamino)-N-(pyridin-3-ylmethyl)nicotinamide (0.10 g, 0.27 mmol), EtOH (2 mL) and stirred with HCl₍g₎ for 20 minutes. The reaction mixture was then concentrated to dryness to give the ethyl 6-(3-fluorophenethylamino)-5-(pyridin-3-ylmethylcarbamoyl)picolinimidate. LC/MS (M+H⁺) m/z 422.1.

A mixture of the ethyl 6-(3-fluorophenethylamino)-5-(pyridin-3-ylmethylcarbamoyl)picolinimidate and NH₃/MeOH (7N, 0.76 mL) was stirred at 50° C. for 1 hour. The reaction mixture was concentrated to dryness to give 6-carbamimidoyl-2-(3-fluorophenethylamino)-N-(pyridin-3-ylmethyl)nicotinamide. LC/MS (M+H⁺) m/z 394.1.

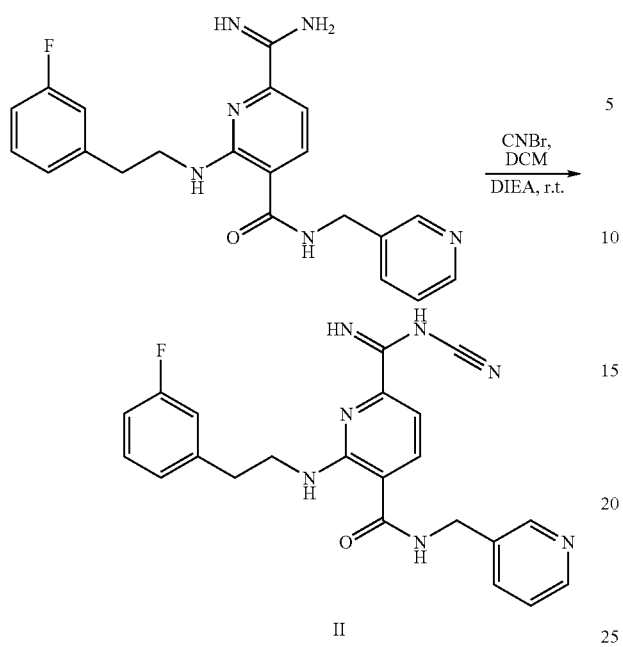

A mixture of 6-carbamimidoyl-2-(3-fluorophenethylamino)-N-(pyridin-3-ylmethyl)nicotinamide (0.013 g, 0.034 mmol), CNBr (3N, 0.017 mL, 0.051 mmol), DIPEA (0.0085 mL, 0.051 mmol), in DCM (0.10 mL) was stirred at room temperature until the reaction was complete. The reaction mixture was concentrated to dryness and purified by RP-HPLC using a mixture of acetonitrile and H₂O to give 6-(N-cyanocarbamimidoyl)-2-(3-fluorophenethylamino)-N-(pyridin-3-ylmethyl)nicotinamide as a solid (0.0058 g, 41%). LC/MS (M+H$^+$) m/z 418.1.

Example III

Using procedures similar to those described herein, the compounds in the following table were synthesized and tested.

| IC50 Arithmetic Mean | Ion | m/z | CHEMICAL NAME |
|---|---|---|---|
| 7.3929 | M + H | 457.1 | N-{[6-(aminomethyl)(2-pyridyl)]methyl}(2-{[2-(3-fluorophenyl)ethyl]amino}-5-(3-pyridyl)(3-pyridyl))carboxamide |
| 9.8364 | M + H | 457.1 | N-{[6-(aminomethyl)(2-pyridyl)]methyl}(2-{[2-(3-fluorophenyl)ethyl]amino}-5-(4-pyridyl)(3-pyridyl))carboxamide |
| 17.7374 | M + H | 460.1 | N-{[6-(aminomethyl)(2-pyridyl)]methyl}(2-{[2-(3-fluorophenyl)ethyl]amino}-5-(1-methylpyrazol-4-yl)(3-pyridyl))carboxamide |
| 6.0282 | M + H | 481.1 | N-{[6-(aminomethyl)(2-pyridyl)]methyl}(5-(2-cyanophenyl)-2-{[2-(3-fluorophenyl)ethyl]amino}(3-pyridyl))carboxamide |
| 12.683 | M + H | 376.1 | (5-cyano-2-{[2-(3-fluorophenyl)ethyl]amino}(3-pyridyl))-N-(2-pyridylmethyl)carboxamide |
| 17.7243 | M + H | 445 | (5-bromo-2-{[2-(3-fluorophenyl)ethyl]amino}(3-pyridyl))-N-[(6-methyl(2-pyridyl))methyl]carboxamide |
| 17.258 | M + H | 465 | (5-bromo-6-chloro-2-{[2-(3-fluorophenyl)ethyl]amino}(3-pyridyl))-N-(2-pyridylmethyl)carboxamide |
| 11.19 | M + H | 341 | 5-bromo-2-{[2-(3-fluorophenyl)ethyl]amino}pyridine-3-carboxylic acid |
| 14.887 | M + H | 300.1 | methyl 5-cyano-2-{[2-(3-fluorophenyl)ethyl]amino}pyridine-3-carboxylate |
| 9.7159 | M + H | 590 | N-({6-[(1,3-dioxobenzo[c]azolin-2-yl)methyl](2-pyridyl)}methyl)(5-bromo-2-{[2-(3-fluorophenyl)ethyl]amino}(3-pyridyl))carboxamide |
| 11.8154 | M + H | 431 | (5-bromo-2-{[2-(3-fluorophenyl)ethyl]amino}(3-pyridyl))-N-(2-pyridylmethyl)carboxamide |
| 15.0424 | M + H | 460 | N-{[6-(aminomethyl)(2-pyridyl)]methyl}(5-bromo-2-{[2-(3-fluorophenyl)ethyl]amino}(3-pyridyl))carboxamide |
| 16.0219 | M + H | 457.1 | N-{[6-(aminomethyl)(2-pyridyl)]methyl}(2-{[2-(3-fluorophenyl)ethyl]amino}-5-(2-pyridyl)(3-pyridyl))carboxamide |
| 44.3072 | M + H | 389.2 | methyl 6-[(4-carbamoylbutyl)amino]-2-{[2-(3-fluorophenyl)ethyl]amino}pyridine-3-carboxylate |
| 55.0688 | M + H | 493.2 | 5-[(6-{[2-(3-fluorophenyl)ethyl]amino}-5-[N-(2-pyridylmethyl)carbamoyl](2-pyridyl))amino]-N,N-dimethylpentanamide |
| 38.046 | M + H | 479.2 | 5-[(6-{[2-(3-fluorophenyl)ethyl]amino}-5-[N-(3-pyridylmethyl)carbamoyl](2-pyridyl))amino]-N-methylpentanamide |

-continued

| IC50 Arithmetic Mean | Ion | m/z | CHEMICAL NAME |
|---|---|---|---|
| 6.7378 | M + H | 465.2 | (6-[(4-carbamoylbutyl)amino]-2-{[2-(3-fluorophenyl)ethyl]amino}(3-pyridyl))-N-(3-pyridylmethyl)carboxamide |
| 70.3134 | M + H | 479.2 | 4-[(6-{[2-(3-fluorophenyl)ethyl]amino}-5-[N-(3-pyridylmethyl)carbamoyl](2-pyridyl))amino]-N,N-dimethylbutanamide |
| 42.7772 | M + H | 451.2 | (6-[(3-carbamoylpropyl)amino]-2-{[2-(3-fluorophenyl)ethyl]amino}(3-pyridyl))-N-(3-pyridylmethyl)carboxamide |
| 4.919 | M + H | 394.1 | (6-(dimethylamino)-2-{[2-(3-fluorophenyl)ethyl]amino}(3-pyridyl))-N-(3-pyridylmethyl)carboxamide |
| 49.2162 | M + H | 556.2 | 5-[(6-{[2-(3-fluorophenyl)ethyl]amino}-5-[N-(3-pyridylmethyl)carbamoyl](2-pyridyl))amino]-N-(3-pyridylmethyl)pentanamide |
| 10.883 | M + H | 380.2 | (2-{[2-(3-fluorophenyl)ethyl]amino}-6-(methylamino)(3-pyridyl))-N-(3-pyridylmethyl)carboxamide |
| 33.5035 | M + H | 422.2 | N-(6-{[2-(3-fluorophenyl)ethyl]amino}-5-[N-(3-pyridylmethyl)carbamoyl](2-pyridyl))-N-methylacetamide |
| 53.412 | M + H | 452.2 | N-(6-{[2-(3-fluorophenyl)ethyl]amino}-5-[N-(3-pyridylmethyl)carbamoyl](2-pyridyl))-N-(2-hydroxyethyl)acetamide |
| 13.9674 | M + H | 394.1 | 6-{[2-(3-fluorophenyl)ethyl]amino}-5-[N-(3-pyridylmethyl)carbamoyl]pyridine-2-carboxamide |
| 65.8061 | M + H | 376.1 | (6-cyano-2-{[2-(3-fluorophenyl)ethyl]amino}(3-pyridyl))-N-(3-pyridylmethyl)carboxamide |
| 5.6092 | M + H | 457.1 | (2-{[2-(3-fluorophenyl)ethyl]amino}-6-[(3-pyridylmethyl)amino](3-pyridyl))-N-(3-pyridylmethyl)carboxamide |
| 0.2309 | M + H | 418.1 | (6-[(cyanoamino)iminomethyl]-2-{[2-(3-fluorophenyl)ethyl]amino}(3-pyridyl))-N-(3-pyridylmethyl)carboxamide |
| 10.5082 | M + H | 405.1 | (6-((1Z)-1-methylprop-1-enyl)-2-{[2-(3-fluorophenyl)ethyl]amino}(3-pyridyl))-N-(3-pyridylmethyl)carboxamide |
| 44.1181 | M + H | 408.1 | (2-{[2-(3-fluorophenyl)ethyl]amino}-6-(N-methylcarbamoyl)(3-pyridyl))-N-(3-pyridylmethyl)carboxamide |
| 4.3507 | M + H | 409.1 | methyl 6-{[2-(3-fluorophenyl)ethyl]amino}-5-[N-(3-pyridylmethyl)carbamoyl]pyridine-2-carboxylate |
| 10.7731 | M + H | 457.2 | (2-{[2-(3-fluorophenyl)ethyl]amino}-6-[(2-pyridylmethyl)amino](3-pyridyl))-N-(3-pyridylmethyl)carboxamide |
| 0.7796 | M + H | 469 | (6-((1E)prop-1-enyl)-5-bromo-2-{[2-(3-fluorophenyl)ethyl]amino}(3-pyridyl))-N-(3-pyridylmethyl)carboxamide |
| 3.4457 | M + H | 449.1 | methyl (2E)-3-(6-{[2-(3-fluorophenyl)ethyl]amino}-5-[N-(3-pyridylmethyl)carbamoyl](2-pyridyl))but-2-enoate |
| 33.9795 | M + H | 457.1 | (2-{[2-(3-fluorophenyl)ethyl]amino}-6-[(4-pyridylmethyl)amino](3-pyridyl))-N-(3-pyridylmethyl)carboxamide |
| 2.6522 | M + H | 423.1 | ethyl 6-{[2-(3-fluorophenyl)ethyl]amino}-5-[N-(3-pyridylmethyl)carbamoyl]pyridine-2-carboxylate |
| 0.3021 | M + H | 391.2 | (6-((1E)prop-1-enyl)-2-{[2-(3-fluorophenyl)ethyl]amino}(3-pyridyl))-N-(3-pyridylmethyl)carboxamide |
| 0.3608 | M + H | 416.1 | (6-((1E)prop-1-enyl)-5-cyano-2-{[2-(3-fluorophenyl)ethyl]amino}(3-pyridyl))-N-(3-pyridylmethyl)carboxamide |
| 0.3473 | M + H | 405.2 | (2-{[2-(3-fluorophenyl)ethyl]amino}-6-(2-methylprop-1-enyl)(3-pyridyl))-N-(3-pyridylmethyl)carboxamide |
| 17.2629 | M + H | 421.2 | (6-[(dimethylamino)iminomethyl]-2-{[2-(3-fluorophenyl)ethyl]amino}(3-pyridyl))-N-(3-pyridylmethyl)carboxamide |
| 5.1875 | M + H | 446.1 | (6-[(1E)-1-(dimethylamino)-2-cyano-2-azavinyl]-2-{[2-(3-fluorophenyl)ethyl]amino}(3-pyridyl))-N-(3-pyridylmethyl)carboxamide |
| 6.619 | M + H | 393.1 | 6-{[2-(3-fluorophenyl)ethyl]amino}-5-[N-(3-pyridylmethyl)carbamoyl]pyridine-2-carboxamidine |
| 14.9996 | M + H | 407.1 | 2-[(2-{[2-(3-fluorophenyl)ethyl]amino}-5-phenyl(3-pyridyl))carbonylamino]-N-methylacetamide |

-continued

| IC50 Arithmetic Mean | Ion | m/z | CHEMICAL NAME |
|---|---|---|---|
| 0.038 | M + H | 420.1 | (6-((1E)prop-1-enyl)-2-{[2-(3-fluorophenyl)ethyl]amino}(3-pyridyl))-N-{[2-(aminomethyl)(3-pyridyl)]methyl}carboxamide |
| 17.9719 | M + H | 432.1 | 2-[(5-(2-cyanophenyl)-2-{[2-(3-fluorophenyl)ethyl]amino}(3-pyridyl))carbonylamino]-N-methylacetamide |
| 0.9273 | M + H | 421.2 | (6-((1E)-3-methoxyprop-1-enyl)-2-{[2-(3-fluorophenyl)ethyl]amino}(3-pyridyl))-N-(3-pyridylmethyl)carboxamide |
| 73.03 | M + H | 423.2 | (6-(ethoxyethyl)-2-{[2-(3-fluorophenyl)ethyl]amino}(3-pyridyl))-N-(3-pyridylmethyl)carboxamide |
| 24.7905 | M + H | 393.1 | (6-acetyl-2-{[2-(3-fluorophenyl)ethyl]amino}(3-pyridyl))-N-(3-pyridylmethyl)carboxamide |
| 0.0805 | M + H | 438.1 | (6-((1E)prop-1-enyl)-5-fluoro-2-{[2-(3-fluorophenyl)ethyl]amino}(3-pyridyl))-N-{[2-(aminomethyl)(3-pyridyl)]methyl}carboxamide |
| 11.7073 | M + H | 538.2 | (6-((1E)prop-1-enyl)-5-fluoro-2-{[2-(3-fluorophenyl)ethyl]amino}(3-pyridyl))-N-[(2-{[(tert-butoxy)carbonylamino]methyl}(3-pyridyl))methyl]carboxamide |
| 2.6897 | M + H | 398 | N-{[2-(aminomethyl)(3-pyridyl)]methyl}(5-fluoro-2-{[2-(3-fluorophenyl)ethyl]amino}(3-pyridyl))carboxamide |
| 26.8336 | M + H | 351.1 | (2-{[2-(3-fluorophenyl)ethyl]amino}(3-pyridyl))-N-(3-pyridylmethyl)carboxamide |
| 2.7696 | M + H | 419.2 | (6-(1,2-dimethylprop-1-enyl)-2-{[2-(3-fluorophenyl)ethyl]amino}(3-pyridyl))-N-(3-pyridylmethyl)carboxamide |
| 8.1803 | M + H | 423.1 | (2-{[2-(3-fluorophenyl)ethyl]amino}-6-(3-methoxypropyl)(3-pyridyl))-N-(3-pyridylmethyl)carboxamide |
| 0.7025 | M + H | 421.2 | (6-(1-ethoxyvinyl)-2-{[2-(3-fluorophenyl)ethyl]amino}(3-pyridyl))-N-(3-pyridylmethyl)carboxamide |
| 13.0601 | M + H | 410.2 | (2-{[2-(3-fluorophenyl)ethyl]amino}-6-[(2-hydroxyethyl)amino](3-pyridyl))-N-(3-pyridylmethyl)carboxamide |
| 45.4109 | M + H | 424.2 | (2-{[2-(3-fluorophenyl)ethyl]amino}-6-[(2-hydroxyethyl)methylamino](3-pyridyl))-N-(3-pyridylmethyl)carboxamide |
| 7.6223 | M + H | 424.2 | (2-{[2-(3-fluorophenyl)ethyl]amino}-6-[(2-methoxyethyl)amino](3-pyridyl))-N-(3-pyridylmethyl)carboxamide |
| 10.4821 | M + H | 438.2 | (2-{[2-(3-fluorophenyl)ethyl]amino}-6-[(2-hydroxypropyl)methylamino](3-pyridyl))-N-(3-pyridylmethyl)carboxamide |
| 11.0022 | M + H | 438.2 | (2-{[2-(3-fluorophenyl)ethyl]amino}-6-[(3-methoxypropyl)amino](3-pyridyl))-N-(3-pyridylmethyl)carboxamide |
| 8.4659 | M + H | 424.2 | (2-{[2-(3-fluorophenyl)ethyl]amino}-6-[(3-hydroxypropyl)amino](3-pyridyl))-N-(3-pyridylmethyl)carboxamide |

Example IV

In Vitro Model of Dose Dependent Smooth Muscle Myosin ATPase Modulation

Screening assays were performed using a pyruvate kinase and lactate dehydrogenase-coupled ATPase assay containing the following reagents: Potassium PIPES (50 mM), $MgCl_2$ (3 mM), KCl (100 mM), ATP (0.15 mM), DTT (1 mM), BSA (0.1 mg/ml), NADH (0.5 mM), PEP (1.5 mM), pyruvate kinase (4 U/ml), lactate dehydrogenase (8 U/ml), and antifoam (50 ppm) (concentrations expressed are final assay concentrations). The pH was adjusted to 6.80 at 22□ C by addition of potassium hydroxide. Lead optimization assays were performed with a more sensitive pyruvate kinase/horseradish peroxidase/pyruvate oxidase-coupled ATPase assay containing the following reagents: Potassium PIPES (12 mM), $MgCl_2$ (2 mM), KCl (100 mM), ATP (0.15 mM), BSA (0.05 mg/ml), potassium phosphate (2 mM), amplex red (0.1 mM), PEP (0.1 mM), pyruvate kinase (4 U/ml), horseradish peroxidase (0.5 U/ml), pyruvate oxidase (0.5 U/ml), and antifoam (50 ppm) (concentrations expressed are final assay concentrations). The pH was adjusted to 7.00 at 22□ C by addition of potassium hydroxide.

The protein components specific to this assay are chicken gizzard smooth muscle myosin subfragment-1 that has been chemically crosslinked to either cardiac or skeletal actin using an excess of 1-Ethyl-3-[3-dimethylaminopropyl]carbodiimide hydrochloride and N-hydroxysuccinimide. The exact concentration of the crosslinked smooth muscle myosin in the assay is determined empirically, by titration to achieve a desired rate of ATP hydrolysis. The concentration varies between protein preparations due to variations in the fraction of active molecules in each preparation.

Compound dose response assays are performed by first preparing a dilution series of test compound, each with an assay mixture containing potassium PIPES, MgCl$_2$, KCl, ATP, BSA, potassium phosphate, amplex red, PEP, crosslinked smooth muscle actomyosin (subfragment-1), antifoam, and water. The assay is started by adding an equal volume of solution containing potassium Pipes, MgCl$_2$, KCl, BSA, potassium phosphate, pyruvate kinase, horseradish peroxidase, pyruvate oxidase, antifoam, and water. ATP hydrolysis is monitored by measuring the fluorescence of amplex red (excitation at 480 nm, emission at 615 nm). The resulting dose response curve is fit by the 4 parameter equation y=Bottom+((Top-Bottom)/(1+((IC$_{50}$/X)^Hill))). The IC$_{50}$ is defined as the concentration at which ATPase activity is midway between the top and bottom of the dose response curve.

Certain chemical entities described herein have an IC$_{50}$ less than 10 μM; for example, less than 1 μM.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of Formula I

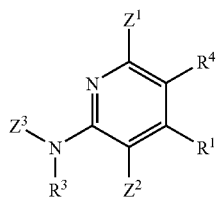

Formula I or a pharmaceutically acceptable salt thereof wherein
R$^1$ and R$^4$ are independently chosen from hydrogen, cyano, halo, and alkyl;
Z$^1$ is chosen from substituted alkyl, optionally substituted alkenyl, and optionally substituted alkynyl;
Z$^2$ is —C(O)NR$^2$R$^5$ wherein R$^2$ is optionally substituted alkyl, and R$^5$ is chosen from hydrogen and alkyl;
Z$^3$ is optionally substituted alkyl; and
R$^3$ is chosen from hydrogen and alkyl.

2. The compound of claim 1 wherein R$^3$ is chosen from hydrogen and methyl.

3. The compound of claim 2 wherein R$^3$ is hydrogen.

4. The compound of claim 1 wherein R$^4$ is chosen from hydrogen, cyano, chloro, bromo, fluoro, and methyl.

5. The compound of claim 1 wherein R$^4$ is hydrogen.

6. The compound of claim 1 wherein R$^5$ is chosen from hydrogen and methyl.

7. The compound of claim 6 wherein R$^5$ is hydrogen.

8. The compound of claim 1 wherein R$^2$ is chosen from optionally substituted methyl, optionally substituted ethyl, optionally substituted propyl, optionally substituted butyl, optionally substituted pentyl, and optionally substituted hexyl, wherein each optionally substituted group is optionally substituted with one, two or three groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

9. The compound of claim 8 wherein R$^2$ is chosen from methyl and ethyl, wherein the methyl and ethyl groups are optionally substituted with one or two groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

10. The compound of claim 9 wherein R$^2$ is chosen from (1-(2-aminoethyl)-1H-pyrazol-3-yl)methyl; (1-(methylsulfonyl)piperidin-3-yl)methyl; (1-acetylpiperidin-3-yl)methyl; (1-acetylpyrrolidin-2-yl) methyl; (1H-imidazol-2-yl) methyl; (1H-pyrazol-3-yl)methyl; (1-methyl-1H-pyrazol-3-yl) methyl; (1-methyl-1H-pyrazol-5-yl)methyl; (2-(aminocarbonyl)ethylamino)carbonylmethyl; (2-(aminomethyl)pyridin-3-yl)methyl; (2-(carboxy)ethylamino)carbonylmethyl; (2-(dimethylamino)ethylamino)carbonylmethyl; (2-(hydroxy)ethylamino)carbonylmethyl; (2-(methylamino)ethylamino)carbonylmethyl; (2-(N-methyl-N-(t-butoxycarbonyl)-amino)ethylamino)carbonylmethyl; (2-oxopiperidin-3-yl) methyl; (3-(dimethylamino)propylamino)carbonylmethyl; (3-(hydroxy)ethylamino)carbonylmethyl; (3-(t-butaxycarbonylamino) propylamino)carbonylmethyl: (4-(aminomethyl)pyridin-2-yl)methyl; (5-(aminomethyl)pyridin-2-yl) methyl; (6((1,3-dioxoisoindolin-2-yl)methyl)pyridin-2-yl) methyl; (6-(2-aminoethylamino)pyridin-2-yl)methyl; (6-(3-aminopropylamino)pyridin-2-yl) methyl; (6-(aminomethyl)pyridin-2-yl)methyl; (6-(hydroxymethyl)pyridin-2-yl)methyl; (6-bromopyridin-2-yl)methyl; (methylsulfonamido)carbonylmethyl; (pyridin-2-yl) ethylamino; 1-(2-(tert-butoxycarbonylamino)ethyl)-1H-pyrazol-3-ylmethyl; 1-(2-(tert-butoxycarbonylamino) ethyl)-1H-pyrazol-5-ylmethyl; 1-(aminocarbonyl)-2-(amino)-eth-1-yl; 1-(aminocarbonyl)-3-(amino)-propyl; 1-(aminocarbonyl)-4-(amino)-butyl; 1-(aminocarbonyl)-4-(benzyloxycarbonylamino)-pentyl; 1-(aminocarbonyl)-5-(amino)-pentyl; 1-(aminocarbonyl) eth-1-yl; 1-(carboxy)-2-(amino)-eth-1-yl; 1-(dimethylaminocarbonyl)-2-(amino)-eth-1-yl; 1-(hydroxy)-2-(aminocarbonylmethylamino)eth-1-yl; 1-(hydroxy)-2-(ethoxycarbonylmethylamino)eth-1-yl; 1-(hydroxy)-2-(pyridin-2-ylmethylamino)eth-1-yl; 1-(methoxycarbonyl)-2-(amino)-eth-1-yl; 1-(methoxycarbonyl)-2-(t-butoxycarbonylamino)-eth-1-yl; 1-(methoxycarbonyl)eth-1-yl; 1-(methylaminocarbonyl)-2-(amino)-eth-1-yl (2 occ); 1-(methylaminocarbonyl)eth-1-yl; 1-aminocarbonyl-2-hydroxy-eth-1-yl; 1-methoxycarbonyl-2-hydroxy-eth-1-yl; 2-(2-aminoethoxy) ethyl; 2-(2-aminoethyl)-pyridin-6-ylmethyl; 2-(2-aminoethylamino)ethyl; 2-(3-fluorophenyl)ethyl; 2-(3-methoxycarbonyl)ethyl; 2-(6-(aminomethyl)pyridin-2-yl)ethyl; 2-(acetylamino)ethyl; 2-(amino)ethyl; 2-(aminocarbonyl)-2-(acetylamino)-eth-1-yl; 2-(aminocarbonyl)-2-(amino)-eth-1-yl; 2-(aminocarbonyl)ethyl; 2-(aminomethyl)pyridin-5-ylmethyl; 2-(carboxy)-2-(amino)-eth-1-yl; 2-(dimethylamino)ethyl; 2-(dimethylaminocarbonyl)-2-(amino)-eth-1-yl; 2-(ethoxycarbonyl)ethyl; 2-(methoxycarbonyl)-2-(acetylamino)-eth-1-yl; 2-(methoxycarbonyl)-2-(amino)-eth-1-yl; 2-(methoxycarbonylamino)ethyl; 2-(methylamino)ethyl; 2-(methylaminocarbonyl)-2-(acetylamino)-eth-1-yl; 2-(methylaminocarbonyl)-2-(amino)eth-1-yl; 2-(methylsulfonamido)ethyl; 2-(methyoxycarbonyl)-2-(amino)eth-1-yl; 2-(N-(t-butoxycarbonyl) -N-(methyl)-amino)ethyl; 2-(piperazin-1-yl)ethyl; 2-(pyrazin-2-yl)ethyl;

2-(pyridin-2-yl)ethyl; 2-(pyridin-3-yl)ethyl; 2-(t-butoxycarbonylaminomethyl)pyridin-3-ylmethyl; 2-(t-butoxycarbonylaminomethyl)pyridin-6-ylmethyl; 2-(trifluoromethyl)-pyridin-6-ylmethyl; 2-aminopyridin-3-ylmethyl; 2-aminopyridin-5-ylmethyl; 2-chloropyridin-5-ylmethyl; 2-cyanopyridin-5-ylmethyl; 2-hydroxy-3-amino-prop-1-yl; 2-hydroxyethyl; 2-methoxyeth -1-yl; 2-methoxypyridin-3-ylmethyl; 2-methoxypyridin-5-ylmethyl: 2-methylpyridin -3-ylmethyl; 2-methylpyridin-5-ylmethyl; 2-methylpyridin-6-ylmethyl; 3-(2-aminoethyl) cyclohexyl)methyl; 3-(4-methylpiperazin-1-yl)propyl; 3-(amino)-3-(methylaminocarbonyl)prop-1-yl; 3-(aminocarbonyl)propyl; 3-(aminomethyl) benzyl; 3-(aminomethyl)pyridin-2-ylmethyl; 3-(methoxycarbonyl)propyl; 3-(methylaminocarbonyl)propyl; 3-(trifluoromethyl)-pyridin-2-ylmethyl; 3,4-difluorobenzyl; 3-aminomethylpyridin-4-ylmethyl; 3-aminopropyl; 3-carbamoylcyclopentyl; 3-carboxypropyl; 3-hydroxypropyl; 3-methoxypropyl; 4-(aminomethyl)-pyridin-2-ylmethyl; 4-(N,N-dimethylamino)pyridin-3-ylmethyl; 4-(t-butoxycarbonylamino)-morpholinomethyl; 4-aminobutyl; 4-aminomethylpyridin-3-ylmethyl; 4-cyanobenzyl; 4-fluorobenzyl; 4-methylaminopyridin -3-ylmethyl; 4-methylbenzyl; 4-morpholinopyridin-3-ylmethyl; 4-piperazinylpyridin -3-ylmethyl; 5-((bis(dimethylamino)methylamino)methyl)pyridin-3-ylmethyl; 5-(aminomethyl) pyridin-2-ylmethyl; 5-(aminomethyl)pyridin-3-ylmethyl; 5-(hydroxymethyl)pyridin-3-ylmethyl; 5-(t-butoxycarbonylaminomethyl)-pyridin-2-ylmethyl; 5-(trifluoromethyl)-pyridin-2-ylmethyl; 5-aminopentyl; 5-aminopyridin-2-ylmethyl; 6-((bis(dimethylamino)methyleneamino)methyl) pyridin-2-yl)methyl; 6-(4-acetylpiperazin-1-yl) pyridin-3-ylmethyl); 6-(aminomethyl)pyridin-2-ylmethyl; 6-aminohexyl; aminocarbonylmethyl; benzyl; cyclopropylmethyl; dimethylaminocarbonylmethyl; isopropyl; isoxazol-5-ylmethyl; methoxycarbonylmethyl; methyl; methylaminocarbonylmethyl; oxazol-2-ylmethyl; piperidin-4-ylmethyl; prop-2-en-1-yl; pyrazin-2-ylmethyl; pyridin-2-ylmethyl; pyridin-2-ylmethyl -N-oxide; pyridin-3-ylmethyl; pyridin-3-ylmethyl -N-oxide; pyridin-4-ylmethyl; thiophen-2-ylmethyl; and thiophen-3-ylmethyl.

11. The compound of claim 1 wherein $Z^3$ is optionally substituted lower alkyl.

12. The compound of claim 11 wherein $Z^3$ is chosen from optionally substituted methyl, optionally substituted ethyl, and optionally substituted propyl wherein the methyl, ethyl and propyl groups are optionally substituted with one or two groups selected from hydroxy, optionally substituted aryl, optionally substituted heteroaryl, optionally substituted heterocycloalkyl, optionally substituted cycloalkyl, and optionally substituted aryloxy.

13. The compound of claim 12 wherein $Z^3$ is chosen from 2-(3-methylphenyl)ethyl, (tetrahydrofuran-2-yl)methyl, 1-hydroxycyclohexylmethyl, 2-(1,3-dioxolan-2-yl)ethyl, 2-(1H-imidazol-4--yl)ethyl, 2-(1--methyl -1H-imidazol-4--yl)ethyl, 2-(1-methylpiperidin-4-yl)ethyl, 2-(2,3-difluorophenyl) ethyl, 2-(2,5-difluorophenyl)ethyl, 2-(2,6-difluorophenyl)ethyl, 2-(2-chlorophenyl) ethyl, 2-(2-cyanophenyl) ethyl, 2-(2-fluorophenyl)ethyl, 2-(2-hydroxyphenyl) ethyl, 2-(2-methoxyphenyl)ethyl, 2-(2-methylphenyl)ethyl, 2-(2-oxoimidazolidin -1-yl)ethyl, 2-(2-oxopiperidin-1-yl)ethyl, 2-(2-oxopyrrolidin-1-yl)ethyl, 2-(3-(trifluoromethyl)phenyl) ethyl, 2-(3,4-difluorophenyl)ethyl, 2-(3,5-difluorophenyl) ethyl, 2-(3,5-dimethyl-1H-pyrazol-1-yl)ethyl, 2-(3,5-dimethyl-1H-pyrazol-4-yl)ethyl, 2-(3-carbamoylphenyl)ethyl, 2-(3-carboxyphenyl)ethyl, 2-(3-cyanophenyl)ethyl, 2-(3-fluorophenyl) -2-(hydroxy)-ethyl, 2-(3-fluorophenyl)ethyl, 2-(3-fluoropyridin-2-yl)ethyl, 2-(3-methoxycarbonylphenyl) ethyl, 2-(3-methoxyphenyl)ethyl, 2-(3-methylphenyl)ethyl, 2-(4-aminophenyl)ethyl, 2-(4-chlorophenyl)ethyl, 2-(4-fluorophenyl)ethyl, 2-(4-hydroxyphenyl) ethyl, 2-(benzo[d][1,3]dioxol-5--yl)ethyl, 2-(furan-2-yl)ethyl, 2-(hydroxy)-2-(phenyl)ethyl, 2-(phenyl)ethyl, 2-(pyridin-2-yl)ethyl, 2-(pyridin-3-yl)ethyl, 2-(thiophen-2-yl) ethyl, 2-cyclohex-1-enylethyl, 2-cyclohexylethyl, 2-morpholinoethyl, 2-phenoxyethyl, 2-phenylprop-1-yl, 3-(1H-imidazol-1-yl)prop-1-yl, 3-phenylpropyl, benzyl, chloro, isopentyl, propyl, pyridin-2-ylmethyl, pyridin-3-ylmethyl, and thiophen-3-ylmethyl.

14. The compound of claim 1 wherein $Z^3$ is chosen from 2-(3-fluorophenyl)ethyl and 2-(pyridin-2-yl)ethyl.

15. The compound of claim 1 wherein $Z^1$ is optionally substituted alkenyl.

16. The compound of claim 1 wherein $Z^1$ is chosen from alkenyl, and alkyl, wherein each group is substituted by one or two groups selected from cyano, halo, hydroxy, formyl, optionally substituted alkyl, optionally substituted alkenyl, optionally substituted alkoxy, carboxyl, optionally substituted alkoxycarbonyl, optionally substituted acyl, optionally substituted aminocarbonyl, optionally substituted heterocycloalkyl, optionally substituted heteroaryl, optionally substituted carbamimidoyl, and optionally substituted sulfonyl.

17. The compound of claim 1 wherein $Z^1$ is chosen from (Z)-but-2-en-2-yl; 1 ethoxyvinyl; 2 methylprop-1-enyl; 3-(methoxycarbonyl)-prop-2-en-2-yl; 3 methoxy-prop-1-enyl; 3 methylbut-2-en-2-yl; and prop-1-enyl.

18. The compound of claim 1 wherein $R^1$ is chosen from hydrogen and methyl.

19. The compound of claim 18 wherein $R^1$ is hydrogen.

20. The compound of claim 1 wherein the compound of Formula I is chosen from (6-((1Z)-1-methylprop-1-enyl)-2-{[2-(3-fluorophenyl)ethyl]amino}(3-pyridyl))-N-(3-pyridylmethyl)carboxamide (6-((1E)prop-1-enyl)-5-bromo-2-{[2-(3-fluoropheny)ethyl]amino}(3-pyridyl))-N -(3-pyridylmethyl)carboxamide, methyl (2E)-3-(6-{[2-(3--fluoropheny)ethyl]amino}-5[N-(3-pyridylmethyl) carbamoyl](2-pyridyl))but-2-enoate, (6-((1E)prop-1-enyl)-2-{[2-(3--fluoropheny)ethyl] amino}(3-pyridyl))-N-(3-pyridylmethyl)carboxamide, (6-((1E)prop-1-enyl)-2-{[2-(3--fluorophenyl)ethyl] amino}(3-pyridyl))-N -3-pyridylmethyl)carboxamide, (2-{[2-(3-fluorophenyl)ethyl]amino}6-(2methylprop-1-enyl)(3-pyridyl))-N-(3(pyridylmethyl)carboxamide, (6-((1E)prop-1-enyl)-2-{[2-(3--fluorophenyl)ethyl] amino}(3-pyridyl))-N-{[2-(aminomethyl)(3-pyridyl)] methyl}carboxamide, (6-((1E)-3-methoxyprop-1-enyl)-2-{[2-(3-fluorophenyl) ethyl]amino}(3-pyridyl))-N-(3-pyridylmethyl)carboxamide, (6-(ethoxyethyl)-2-{[2-(3-fluorophenyl)ethyl]amino}(3-pyridyl))-N-(3-pyridylmethyl)carboxamide, (6-((1E)prop-1-enyl)-5-fluoro-2-{[2-(3-fluorophenyl) ethyl]amino}(3-pyridyl))-N-{[2-(aminomethyl)(3-pyridyl)]methyl}carboxamide, (6-((1E)prop-1-enyl)-5-fluoro-2-{[2-(3-fluorophenyl) ethyl]amino}(3-pyridyl))-N-[(2-{[(tert-butoxy)carbonylamino]methyl}(3-pyridyl))methyl]carboxamide, (6-(1,2-dimethylprop-1-enyl)-2-{[2-(3-fluorophenyl) ethyl]amino}(3-pyridyl))-N-(3-pyridylmethyl)carboxamide, (2-{[2-(3--fluorophenyl)ethyl]amino}-6-(3-methoxypropyl)(3-pyridyl))-N-(3-pyridylmethyl)carboxamide, and (6-(1-ethoxyvinyl)-2-{[2-(3-fluorophenyl)ethyl]amino} (3-pyridyl))-N-(3-pyridylmethyl)carboxamide, or a pharmaceutically acceptable salt thereof.

21. The compound of claim 1, wherein $R^2$ is optionally substituted pyridylmethyl.

22. The compound of claim 21, wherein $R^2$ is optionally substituted 3-pyridylmethyl.

23. The compound of claim 22, wherein $R^2$ is chosen from 3-pyridylmethyl, [2-(aminomethyl)(3-pyridyl)]methyl, and (2-{[(tert-butoxy)carbonylamino]methyl}(3-pyridyl))methyl.

24. The compound of claim 1, wherein $Z^1$ is alkyl substituted with one or two groups chosen from hydroxyl and optionally substituted alkoxy.

25. The compound of claim 24, wherein $Z^1$ is chosen from 1-ethoxyeth-1-yl and 3-methoxypropyl.

26. The compound of claim 1, wherein $Z^3$ is methyl or ethyl substituted with a group chosen from optionally substituted aryl and optionally substituted heteroaryl.

27. The compound of claim 26, wherein $Z^3$ is methyl or ethyl substituted with a group chosen from optionally substituted phenyl and optionally substituted pyridyl.

28. The compound of claim 27, wherein $Z^3$ is ethyl substituted with a group chosen from optionally substituted phenyl and optionally substituted pyridyl.

29. The compound of claim 1 wherein
$R^1$ is hydrogen;
$R^2$ is optionally substituted pyridylmethyl;
$Z^1$ is optionally substituted alkenyl; and
$Z^3$ is methyl or ethyl substituted with a group chosen from optionally substituted aryl and optionally substituted heteroaryl.

30. The compound of claim 29, wherein $Z^3$ is ethyl substituted with a group chosen from optionally substituted phenyl and optionally substituted pyridyl.

31. The compound of claim 30, wherein $R^4$ is hydrogen.

32. A pharmaceutically acceptable composition comprising a pharmaceutically acceptable carrier and a compound of claim 1 or a pharmaceutically acceptable salt thereof.

33. The pharmaceutical composition of claim 32 wherein the composition is formulated in a form chosen from a tablet, capsule, powder, liquid, suspension, suppository and aerosol.

34. A packaged pharmaceutical composition comprising a pharmaceutical composition of claim 32 and instructions for using the composition to treat a patient suffering from a disease associated with smooth muscle myosin or non-muscle myosin.

35. The packaged pharmaceutical composition of claim 34 wherein the disease associated with smooth muscle myosin is selected from hypertension, asthma, chronic obstructive pulmonary disease (copd) asthma, bronchoconstrictive disease, glaucoma and other ocular indications, incontinence and other bladder dysfunctions, irritable bowel syndrome, pre-term labor, esophageal dysmotility, strokes, subarachnoid hemorrhages, pre-menstrual cramps, erectile dysfunction and other acute and chronic diseases and conditions associated with smooth muscle myosin and/or non-muscle myosin.

36. A method of treating a disease associated with smooth muscle myosin or non-muscle myosin in a mammal which method comprises administering to a mammal in need thereof a therapeutically effective amount of a compound of claim 1 or a pharmaceutically acceptable salt thereof wherein said disease associated with smooth muscle myosin is selected from hypertension, asthma, chronic obstructive pulmonary disease (copd) asthma, bronchoconstrictive disease, glaucoma and other ocular indications, incontinence and other bladder dysfunctions, irritable bowel syndrome, pre-term labor, esophageal dysmotility, strokes, subarachnoid hemorrhages, pre-menstrual cramps, and erectile dysfunction.

* * * * *